US012746293B2

(12) United States Patent
Kulkarni et al.

(10) Patent No.: US 12,746,293 B2
(45) Date of Patent: Sep. 29, 2026

(54) DNA VECTOR DELIVERY USING LIPID NANOPARTICLES

(71) Applicant: NanoVation Therapeutics Inc., Vancouver (CA)

(72) Inventors: Jayesh Kulkarni, Vancouver (CA); Daniel Kurek, Vancouver (CA); Anthony C. Y. Tam, Vancouver (CA); Kate E. R. Hollinshead, Vancouver (CA); Dominik Witzigmann, Binzen (DE)

(73) Assignee: NanoVision Therapeutics Inc., Vancouver (CA)

(*) Notice: Subject to any disclaimer, the term of this patent is extended or adjusted under 35 U.S.C. 154(b) by 180 days.

(21) Appl. No.: 18/565,603

(22) PCT Filed: Jun. 1, 2022

(86) PCT No.: PCT/CA2022/050877
§ 371 (c)(1),
(2) Date: Nov. 30, 2023

(87) PCT Pub. No.: WO2022/251959
PCT Pub. Date: Dec. 8, 2022

(65) Prior Publication Data

US 2024/0269323 A1 Aug. 15, 2024

Related U.S. Application Data

(60) Provisional application No. 63/202,210, filed on Jun. 1, 2021.

(51) Int. Cl.
*A61K 48/00* (2006.01)
*A61K 9/1272* (2025.01)
*A61K 9/51* (2006.01)
*C12N 15/88* (2006.01)

(52) U.S. Cl.
CPC ........ *A61K 48/0041* (2013.01); *A61K 9/1272* (2013.01); *A61K 9/5123* (2013.01); *C12N 15/88* (2013.01)

(58) Field of Classification Search
None
See application file for complete search history.

(56) References Cited

U.S. PATENT DOCUMENTS

| | | | |
|---|---|---|---|
| 7,514,099 B2 | 4/2009 | Chen et al. | |
| 7,901,708 B2 | 3/2011 | Maclachlan et al. | |
| 8,058,069 B2 | 11/2011 | Yaworski et al. | |
| 8,492,359 B2 | 7/2013 | Yaworski et al. | |
| 8,822,668 B2 | 9/2014 | Yaworski et al. | |
| 9,301,923 B2 | 4/2016 | Baryza et al. | |
| 9,364,435 B2 | 6/2016 | Yaworski et al. | |
| 9,504,651 B2 | 11/2016 | Maclachlan et al. | |
| 9,878,042 B2 | 1/2018 | Yaworski et al. | |
| 10,653,780 B2 | 5/2020 | Hope et al. | |
| 10,703,789 B2 | 7/2020 | Fougerolles et al. | |
| 10,772,975 B2 | 9/2020 | Bancel et al. | |
| 10,898,574 B2 | 1/2021 | Fougerolles et al. | |
| 11,141,378 B2 | 10/2021 | Yaworski et al. | |
| 11,191,849 B2 | 12/2021 | Abrams et al. | |
| 11,219,634 B2 | 1/2022 | Prieve et al. | |
| 11,229,609 B2 | 1/2022 | Cheng et al. | |
| 11,291,734 B2 | 4/2022 | Guild et al. | |
| 11,338,044 B2 | 5/2022 | Guild et al. | |
| 11,547,764 B2 | 1/2023 | Guild et al. | |
| 11,564,998 B2 | 1/2023 | Fougerolles et al. | |
| 12,365,921 B2 * | 7/2025 | Sato | C12N 15/88 |
| 2006/0051405 A1 | 3/2006 | Maclachlan et al. | |
| 2006/0240554 A1 | 10/2006 | Chen et al. | |
| 2008/0188675 A1 | 8/2008 | Chen et al. | |

(Continued)

FOREIGN PATENT DOCUMENTS

| | | |
|---|---|---|
| CA | 2731173 A1 | 2/2010 |
| CA | 2764832 A1 | 12/2010 |

(Continued)

OTHER PUBLICATIONS

Albertsen et al., "The role of lipid components in lipid nanoparticles for vaccines and gene therapy", Advanced Drug Delivery Reviews, 2022, 188:114416.

Ambegia et al., "Stabilized plasma-lipid particles containing PEG-diacylglycerols exhibit extended circulation lifetimes sand tumor selective gene expression", Biochimica et Biophysica Acta, 2005, 1669:155-163.

Brockerhoff and Ramsammy, "Preparation and Structural Studies of Cholesterol Bilayers", Biochimica et Biophysica Acta, 1982, 691:227-232.

Buse and El-Aneed, "Properties, engineering and applications of lipid-based nanoparticle drug-delivery systems: current research and advances", Nanomedicine, 2010, 5(8):1237-1260.

(Continued)

*Primary Examiner* — Brian J Davis
(74) *Attorney, Agent, or Firm* — Lamson IP

(57) ABSTRACT

The present disclosure provides a lipid nanoparticle comprising encapsulated DNA vector and 30 to 60 mol % of a neutral lipid selected from sphingomyelin and a phosphatidylcholine lipid, and at least one of a sterol and a hydrophilic polymer-lipid conjugate, the lipid nanoparticle comprising a core comprising an electron dense region and an aqueous portion surrounded at least partially by a lipid layer comprising a bilayer and the lipid nanoparticle exhibiting at least a 10% increase in gene expression in a disease site or the liver, spleen or bone marrow at any time point after 24 or 48 hours post-injection as compared to a lipid nanoparticle encapsulating DNA vector with an Onpattro-type formulation of ionizable lipid/DSPC/cholesterol/PEG-lipid at 50/10/38.5/1.5, mol:mol, wherein the gene expression is measured in an animal model by detection of green fluorescent protein (GFP) or luciferase. Further provided are methods of medical treatment and uses of such lipid nanoparticles.

24 Claims, 20 Drawing Sheets

(56) References Cited

U.S. PATENT DOCUMENTS

| | | | |
|---|---|---|---|
| 2010/0285112 | A1 | 11/2010 | Novobrantseva et al. |
| 2011/0111044 | A1 | 5/2011 | Zhao et al. |
| 2012/0308663 | A1 | 12/2012 | Roger et al. |
| 2015/0140069 | A1 | 5/2015 | Hong et al. |
| 2018/0085474 | A1 | 3/2018 | Almarsson et al. |
| 2019/0314291 | A1 | 10/2019 | Besin et al. |
| 2020/0078313 | A1 | 3/2020 | Roy et al. |
| 2020/0129445 | A1 | 4/2020 | Patel et al. |
| 2021/0145982 | A1 | 5/2021 | Hoge et al. |
| 2021/0267895 | A1 | 9/2021 | Yaworski et al. |
| 2021/0346306 | A1 | 11/2021 | Dimitrov et al. |
| 2022/0071916 | A1 | 3/2022 | Cheng et al. |
| 2022/0218614 | A1 | 7/2022 | Ali et al. |
| 2022/0280427 | A1 | 9/2022 | Su et al. |
| 2024/0065982 | A1 | 2/2024 | Heyes et al. |

FOREIGN PATENT DOCUMENTS

| | | | | |
|---|---|---|---|---|
| CA | 2486007 | C | 11/2011 | |
| CA | 3103528 | A1 | 12/2019 | |
| CA | 3111483 | A1 | 3/2020 | |
| CA | 3111484 | A1 | 3/2020 | |
| EP | 626169 | B1 | 7/1999 | |
| WO | WO 2010/014895 | A2 * | 2/2010 | ............ A61K 48/00 |
| WO | 2010129687 | | 11/2010 | |
| WO | 2018089540 | A1 | 5/2018 | |
| WO | 2019067992 | A1 | 4/2019 | |
| WO | 2019089828 | A1 | 5/2019 | |
| WO | 2019226650 | | 11/2019 | |
| WO | 2020051223 | A1 | 3/2020 | |
| WO | 2020072324 | A1 | 4/2020 | |
| WO | WO 2020/241679 | A1 * | 12/2020 | .............. B82Y 5/00 |
| WO | 2024086929 | A1 | 5/2024 | |
| WO | WO2025049606 | A1 | 3/2025 | |

OTHER PUBLICATIONS

Cheng and Lee, "The role of helper lipids in lipid nanoparticles (LNPs) designed for oligonucleotide delivery", Advanced Drug Delivery Reviews, 2016, 99:129-137.

Cheng et al., "Selective Organ Targeting (SORT) nanoparticles for tissue specific mRNA delivery and CRISPR/Cas gene editing", Nat. Nanotechnol., Apr. 2020, 15(4): 313-320.

Dabkowska et al., "The effect of neutral helper lipids on the structure of cationic lipid monolayers", J. R. Soc. Interface, 2012, 9:548-561.

Drummond et al., "Optimizing Liposomes for Delivery of Chemotherapeutic Agents to Solid Tumors", Pharmacological Reviews, 1999, 51(4):691-743.

Evers et al., "State-of-the-Art Design and Rapid Mixing Production Techniques of Lipid Nanoparticles for Nucleic Acid Delivery", Nucleic Acid Delivery, Small Methods, 2018, 2:1700375.

Fenton et al., "Customizable lipid nanoparticle materials for the delivery of siRNAs and mRNAs", Angew. Chem. Int. Ed., 2018, 57:13582-13586.

Foglia et al., "Structural Studies of the Monolayers and Bilayers Formed by a Novel Cholesterol-Phospholipid Chimera", Langmuir, 2011, 27:8275-8281.

Han et al., "An ionizable lipid toolbox for RNA delivery", Nature Communications, 2021, 12:7233.

Hayes et al., "Genospheres: self-assembling nucleic acid-lipid nanoparticles suitable for targeted gene delivery", Gene Therapy, 2006, 13:646-651.

Hecker et al., "Non-Viral DNA and mRNA Gene Delivery to the CNS Pre-Operatively for Neuroprotection and Following Neurotrauma", Molecular Therapy, 2004, 9(1):S258.

Hess et al., Vaccination with mRNAs encoding tumor-associated antigens and granulocyte-macrophage colony-stimulating factor efficiently primes CTL responses, but is insufficient to overcome tolerance to a model tumor/self antigen, Cancer Immunol. Immunother., 2006, 55:672-683.

Iman et al., "Characterization of the colloidal properties, in vitro antifungal activity, antileishmanial activity and toxicity in mice of a distagmasterylhemisuccinoyl-glycero-phosphocholine liposome-intercalated amphotericin B", International Journal of Pharmaceutics, 2011, 408:163-172.

International Search Report and the Written Opinion for PCT/CA2023/051416, Oct. 25, 2023.

International Search Report and Written Opinion for PCT/CA2022/050877, Jun. 1, 2021.

International Search Report and Written Opinion for PCT/CA2023/050439, May 26, 2023.

International Search Report and Written Opinion for PCT/CA2023/051632, Apr. 5, 2024.

Jeffs et al., "A scalable, extrusion-free method for efficient liposomal encapsulation of plasmid DNA", Pharmaceutical Research, 2005, 22(3):362-372.

Jung et al., "Lipid nanoparticles for delivery of RNA therapeutics: Current status and the role of in vivo imaging", Theranostics, 2022, 12(17):7509-7531.

Kauffman et al., "Optimization of Lipid Nanoparticle Formulations for mRNA Delivery in Vivo with Fractional Factorial and Definitive Screening Designs", Nano Lett, 2015, 15(11):7300-7306.

Koynova and Tenchov, "Recent Patents on Cationic Lipid Carriers for Delivery of Nucleic Acid", Recent Patents on DNA & Gene Sequences, 2011, 5:8-27.

Kubota et al., "Effect of the nanoformulation of siRNA-lipid assemblies on their cellular uptake and immune stimulation", International Journal of Nanomedicine, 2017, 12:5121-5133.

Kulkarni et al., "Design of lipid nanoparticles for in vitro and in vivo delivery of plasmid DNA", Nanomedicine: Nanotechnology, Biology, and Medicine, 2017, 13:1377-1387.

Kulkarni et al., "Lipid nanoparticles enabling gene therapies: from concepts to clinical utility", Nucleic Acid Therapeutics, 2018, 28(3):146-157.

Kulkarni et al., "On the Formation and Morphology of Lipid Nanoparticles Containing Ionizable Cationic Lipids and siRNA", ACS Nano, 2018, 12:4787-4795.

Kulkarni et al., "On the role of helper lipids in lipid nanoparticle formulations of siRNA", Nanoscale, 2019, 11:21733-21739.

Leung et al., "Microfluidic mixing: a general method for encapsulating macromolecules in lipid nanoparticle structures", The Journal of Physical Chemistry, 2015, 119:8698-8607.

Leung, "Biophysical characterization of lipid nanoparticles containing nucleic acid polymers as produced by microfluidic mixing", A Thesis Submitted in Partial Fulfillment of the Requirements for Degree of Doctor of Philosophy of the Faculty of Graduate and Postdoctoral Studies, the University of British Columbia, Aug. 2014, copyright Alex Kar Kei Leung.

Martinon, "Induction of virus-specific cytotoxic T lymphocytes in vivo by liposome-entrapped mRNA", Eur. J. Immunol., 1993, 23:1719-1722.

Mochizuki et al., "The role of the helper lipid dioleoylphosphatidylethanolamine (DOPE) for DNA transfection cooperating with a cationic lipid bearing ethylenediamine", Biochimica et Biophysica Acta, 2013, 1828:412-418.

Mockey et al., "mRNA-based cancer vaccine: prevention of B16 melanoma progression and metastasis by systemic injection of MART1 mRNA histidylated lipoplexes", Cancer Gene Therapy, 2007, 14:802-814.

Niculescu et al., "New Applications of Lipid and Polymer-Based Nanoparticles for Nucleic Acids Delivery", Pharmaceutics, 2021, 13:2053.

Non-Final Office Action for U.S. Appl. No. 18/194,084, Aug. 16, 2023.

Ordobadi, "Lipid nanoparticles for delivery of bioactive moledules", A Thesis submitted in partial fulfillment of the requirements for the degree of doctor of philosophy in The Faculty of Graduate and Postdoctoral Studies (Biochemistry and Molecular Biology) at the University of British Columbia, Vancouver, British Columbia, Nov. 2019.

Pascola, "Vaccination with Messenger RNA (mRNA)", Toll-like Receptors (TLRs) and Innate Immunity, In Handbook of Experi-

(56) References Cited

OTHER PUBLICATIONS mental Pharmacology, Eds. S. Bauer and G. Hartmann, Springer-Verlag Berlin Heidelberg, 2008, 183:221-235.
Patel et al., "Naturally-occurring cholesterol analogues in lipid nanoparticles induce polymorphic shape and enhance sintracellular delivery of mRNA", Nature Communications, 2020, 11(1):3435.
Pozzi et al., "Transfection efficiency boost of cholesterol-containing lipoplexes", Biochimica et Biophysica Acta, 2012, 1818:2335-2343.
Roces et al., "Manufacturing considerations for the development of lipid nanoparticles using microfluidics", Pharmaceutics, 2020, 12:1095.
Sakurai et al., "Effects of erythrocytes and serum proteins on lung accumulation of lipoplexes containing cholesterol or DOPE as a helper lipid in the single-pass rat lung perfusion system", European Journal of Pharmaceutics and Biopharmaceutics, 2001, 52:165-172.
Sato et al., "Hydrophobic scaffolds of pH-sensitive cationic lipids contribute to miscibility with phospholipids and improve the efficiency of delivering short interfering RNA by small-sized lipid nanoparticles", Acta Biomaterialia, 2020, 102:341-350.
Shoenmaker et al., "mRNA lipid nanoparticle COVID-19 vaccines: structure and stability", International Journal of Pharmaceutics, 2021, 601:120586.
Su et al., "In Vitro and In Vivo mRNA Delivery Using Lipid-Enveloped pH-Responsive Polymer Nanoparticles", Molecular Pharmaceutics, 2011, 8:774-787.
Tam et al., "Stabilized plasmid-lipid particles for systemic gene therapy", Gene Therapy, 2000, 7:1867-1874.
Tenchov et al., "Cubic Phases in Phosphatidylcholine-cholesterol mixtures: Cholesterol as Membrane 'Fusogen'", Biophysical Journal, 2006, 91:2508-2516.
Tenchov et al., "Lipid Nanoparticles—From Liposomes to mRNA Vaccine Delivery, a Landscape of Research Diversity and Advancement", ACS Nano, 2021, 15:16982-17015.
Yamamoto et al., "Current prospects for mRNA delivery", European Journal of Pharmaceutics and Biopharmaceutics, 2009, 71:484-489.
Supplementary European Search Report for Application No. 2281468.6, Apr. 8, 2025, European Patent Office.
European Patent Office, Supplementary European Search Report for European Application No. 22814648.6, Apr. 8, 2025.
Zhang et al., "Helper lipid structure influences protein adsorption and delivery of lipid nanoparticles to spleen and liver", Biomater. Sci., 2021, 9:1449-1463.
Yoshioka et al., "Cationic liposomes-mediated plasmid DNA delivery in murine hepatitis induced by carbon tetrachloride", Journal of Liposome Research, 2009, 19(2):141-147.
Yuan et al., "Ternary nanoparticles of anionic lipid nanoparticles/protamine/DNA for gene delivery", Int J Pharm, 2010, 392(1-2):224-31.
Zhang et al., "Helper lipid structure influences protein adsorption and delivery of lipid nanoparticles to spleen and liver", Biomater. Sci, 2021, 9:1449-1463, Supplementary Information.

* cited by examiner

DNA VECTOR DELIVERY USING LIPID NANOPARTICLES

CROSS-REFERENCE TO RELATED APPLICATIONS

This application claims priority from U.S. Ser. No. 63/202,210 filed on Jun. 1, 2021, which is incorporated herein by reference in its entirety.

TECHNICAL FIELD

The present disclosure relates to a lipid nanoparticle formulation for delivery of DNA vector.

BACKGROUND

Vector DNA is found naturally as small circular, double-stranded DNA molecules in bacteria, although such genetic material is also found in archaea and eukaryotic organisms. Historically, vector DNA has been used as a lab tool for expression of a protein of interest. Expression of an encoded DNA vector from a host organism allows for a given protein or peptide sequence to be produced, isolated and characterized in the laboratory with ease.

DNA vectors are increasingly being studied to examine their utility in gene therapy to treat disease. Such therapy may involve administration of DNA vectors to a patient in need of a therapy comprising a protein or peptide encoded by the DNA. However, the limited ability of DNA vector-based gene therapy to target a disease site has precluded its use in medical applications. Degradation of the DNA vector before reaching a target site remains a problem that limits its clinical utility. Even if a DNA vector reaches a disease site, its inability to become internalized in a target cell severely limits its therapeutic effect.

Lipid nanoparticle (LNP) systems stably encapsulating DNA vector have been described (see U.S. Pat. No. 5,981,501). However, systems that facilitate uptake into target cells and encourage cytosolic release of encapsulated DNA vector and its entry into the nucleus are required for clinical utility to be realized. Most recent work on LNP gene delivery systems for intravenous administration has investigated gene expression in the liver with a focus primarily on developing improved ionizable cationic lipids (Semple et al., 2010, Nat Biotechnol., 28(2):172-6). An example of a clinically approved LNP system for small interfering (siRNA) delivery uses the "Onpattro" lipid composition (ionizable lipid/DSPC/cholesterol/PEG-lipid; 50/10/38.5/1.5; mol:mol) but most of the dose accumulates in the liver within 30 min after administration (Akinc et al., 2019, Nat Nanotechnol., 14(12): 1084-1087). Nonetheless, Onpattro™ is still considered the gold standard for comparison in studies of LNP-mediated efficacy and current approaches to LNP design make few deviations from the four-component system. The incorporation of various permanently positively charged lipids can enhance transfection in a number of extrahepatic tissues following i.v. administration. Unfortunately, such lipids can pose toxicity risk, which may limit clinical applications of such LNPs. Furthermore, the amino lipids used in LNP formulations are optimized for endosomal uptake and release into the cytosol of a cell, but such systems do not allow nuclear delivery. The inability of DNA vector to cross a nuclear membrane is a significant limitation in gene expression systems (Kulkarni et al., 2017, Nanomedicine: Nanotechnology, Biology, and Medicine, 13:1377-1387).

Studies have found that the neutral lipid, distearoylphosphatidylcholine (DSPC) and cholesterol contribute to the stable encapsulation of siRNA in LNPs (Kulkarni et al., 2019, Nanoscale, 11:21733-21739). Despite these findings, in vivo studies have failed to show any clear benefit resulting from adjusting the levels of DSPC in LNPs to improve the extra-hepatic delivery of siRNA. These studies examined extrahepatic siRNA gene silencing in vivo with a four-component LNP having 10 mol % DSPC (MC3 ionizable lipid/Chol/DSPC/PEG-DMP; 50/38.5/10/1.5 mol:mol) or 40 mol % DSPC (MC3/Chol/DSPC/PEG-DMG; 18.5/40/40/1.5 mol:mol) (Ordobadi, 2019, "Lipid Nanoparticles for Delivery of Bioactive Molecules", A Thesis Submitted in Partial Fulfillment of the Requirements for the Degree of Doctor of Philosophy. The University of British Columbia). It was shown that the 10 mol % DSPC (Onpattro™ formulation) had similar liver accumulation and blood circulation lifetimes as the 40 mol % DSPC formulations. Further, the 40 mol % DSPC siRNA-containing LNP (siRNA-LNP) only performed comparably to 10 mol % DSPC formulations in bone marrow gene silencing.

Thus, there is a need in the art for biocompatible and transfection competent LNPs for DNA vector delivery. Such LNPs most advantageously will deliver DNA vector to a broader range of tissues or organs beyond the liver and display enhanced in vivo gene expression of DNA vector at such target sites relative to known formulations. In addition, there is a need in the art for LNPs that are able to target rapidly dividing cells.

The present disclosure seeks to address one or more of these needs and/or provide useful alternatives to DNA vector formulations over those described in the art.

SUMMARY

Lipid nanoparticles (LNPs) prepared in accordance with the disclosure may be especially suitable for enhanced gene expression in a broader range of target sites than previous formulations, thereby expanding the clinical utility of DNA vector-based therapeutics.

In one embodiment, the present disclosure is based, in part, on the finding that LNPs for delivery of DNA vector formulated with elevated levels of neutral lipid, such as a phosphtidylcholine lipid or sphingomyelin, may exhibit vector trapping efficiencies, that are suitable for in vivo delivery. Lipid nanoparticles having elevated levels of neutral lipid may exhibit improved delivery to hepatic and extrahepatic cells, tissues or organs. In some embodiments, such LNPs may be particularly suitable for delivery to target sites affected by a disease or disorder that exhibits high rates of cellular proliferation, such as cancer or pulmonary disease. Bodily sites having high rates of cellular proliferation that may be targeted by the LNPs of the present disclosure also encompass developing tissues including embryonic cells and the like.

According to one aspect of the disclosure, there is provided a lipid nanoparticle comprising encapsulated DNA vector and 30 to 60 mol % of a neutral lipid selected from sphingomyelin and a phosphatidylcholine lipid, and at least one of a sterol and a hydrophilic polymer-lipid conjugate, the lipid nanoparticle comprising a core having an electron dense region and optionally an aqueous portion surrounded at least partially by a lipid layer and the lipid nanoparticle exhibiting at least a 10% increase in gene expression in a disease site, such as a tumor, or the liver, spleen and/or bone marrow at any time point 48 hours post-injection as compared to a lipid nanoparticle encapsulating the DNA vector with an Onpattro-type formulation of ionizable lipid/DSPC/cholesterol/PEG-lipid at 50/10/38.5/1.5, mol:mol, wherein the gene expression is measured in an animal model by detection of a green fluorescent protein (GFP).

According to another aspect of the disclosure, there is provided a lipid nanoparticle for hepatic or extrahepatic delivery of DNA vector, the lipid nanoparticle comprising: (i) encapsulated DNA vector; (ii) a neutral lipid content of from 30 mol % to 60 mol % of total lipid present in the lipid nanoparticle, the neutral lipid selected from sphingomyelin and a phosphatidylcholine lipid; (iii) a cationic lipid content of from 5 mol % to 50 mol % of the total lipid; (iv) a sterol selected from cholesterol or a derivative thereof; and (v) a hydrophilic polymer-lipid conjugate that is present at 0.5 mol % to 5 mol %, or at 0.5 mol % to 3 mol % of the total lipid, the lipid nanoparticle having a core comprising an electron dense region and optionally an aqueous portion that is at least partially surrounded by a lipid layer.

According to a further aspect of the disclosure, there is provided a lipid nanoparticle comprising encapsulated DNA vector and 30 to 60 mol % of a neutral lipid selected from sphingomyelin and a phosphatidylcholine lipid, and at least one of a sterol and a hydrophilic polymer-lipid conjugate, the lipid nanoparticle comprising a core having an electron dense region and optionally an aqueous portion, the core surrounded at least partially by a lipid layer and the lipid nanoparticle exhibiting at least a 10% increase in gene expression in a disease site or in the liver, spleen, lung and/or bone marrow at any one time point greater than 24 or 48 hours post-injection as compared to a lipid nanoparticle encapsulating the DNA vector with an Onpattro-type formulation of ionizable lipid/DSPC/cholesterol/PEG-lipid at 50/10/38.5/1.5, mol:mol, wherein the gene expression is measured in an animal model by detection of luciferase.

According to any of the foregoing aspects, the phosphatidylcholine lipid may be distearoylphosphatidylcholine (DSPC) or 1,2-dioleoyl-sn-glycero-3-phosphocholine (DOPC).

According to any of the foregoing aspects, the neutral lipid may be sphingomyelin.

In another embodiment, the neutral lipid content is between 30 mol % and 50 mol % of the total lipid in the lipid nanoparticle. In yet a further embodiment, the neutral lipid content is between 40 mol % and 60 mol % of total lipid.

In another embodiment, the electron dense region is visualized by cryo-EM microscopy. In yet a further embodiment, the lipid nanoparticle is part of a preparation of lipid nanoparticles, and wherein at least 20% of the lipid nanoparticles are either (i) enveloped by the aqueous portion, or (ii) partially surrounded by the aqueous portion and wherein a portion of a periphery of the electron dense region is contiguous with the lipid layer comprising at least a bilayer, as visualized by cryo-EM microscopy.

In a further embodiment, at least a portion of the DNA vector is encapsulated in the electron dense region or the lipid bilayer.

According to another embodiment, the lipid nanoparticle is part of a preparation of lipid nanoparticles and wherein at least 20% of the lipid nanoparticles as visualized by cryo-EM are elongate in shape.

In a further embodiment, the cationic lipid is an amino lipid. In another embodiment, the cationic lipid has the structure of Formula A, B or C herein.

In another embodiment, the hydrophilic polymer-lipid conjugate is a polyethyleneglycol-lipid conjugate.

In certain embodiments, the sterol is present at from 15 mol % to 50 mol % based on the total lipid present in the lipid nanoparticle. In a further embodiment, the sterol is present at from 18 mol % to 45 mol % based on the total lipid present in the lipid nanoparticle.

In another aspect, there is provided a method for in vivo delivery of DNA vector to a bodily site to treat or prevent a disease or disorder in a mammalian subject, the method comprising: administering to the mammalian subject a lipid nanoparticle of any one of the foregoing embodiments.

The present disclosure also provides use of the lipid nanoparticle of any one of the foregoing aspects or embodiments for in vivo delivery of DNA vector to a bodily site to treat or prevent a disease or disorder in a mammalian subject.

A further aspect of the disclosure provides use of the lipid nanoparticle of any one of the foregoing embodiments for the manufacture of a medicament for in vivo delivery of the DNA vector to a bodily site to treat or prevent a disease or disorder in a mammalian subject.

In one embodiment, the bodily site comprises cells that divide rapidly. In one embodiment, the cells at the target site are dividing at a rate that is at least 30% greater than surrounding parenchymal cells. In another embodiment, the mammalian subject is a fetus.

According to a further embodiment the lipid nanoparticle is for delivery to spleen, bone marrow or liver. In a further embodiment, the lipid nanoparticle is for delivery to the lungs.

In yet a further embodiment, the disease or disorder is a viral infection, cancer, congenital disorder or disease or a cardiovascular disease.

In one embodiment, the lipid nanoparticle is administered intravenously or by administration, such as by injection, directly to a disease site.

Figure 1A:
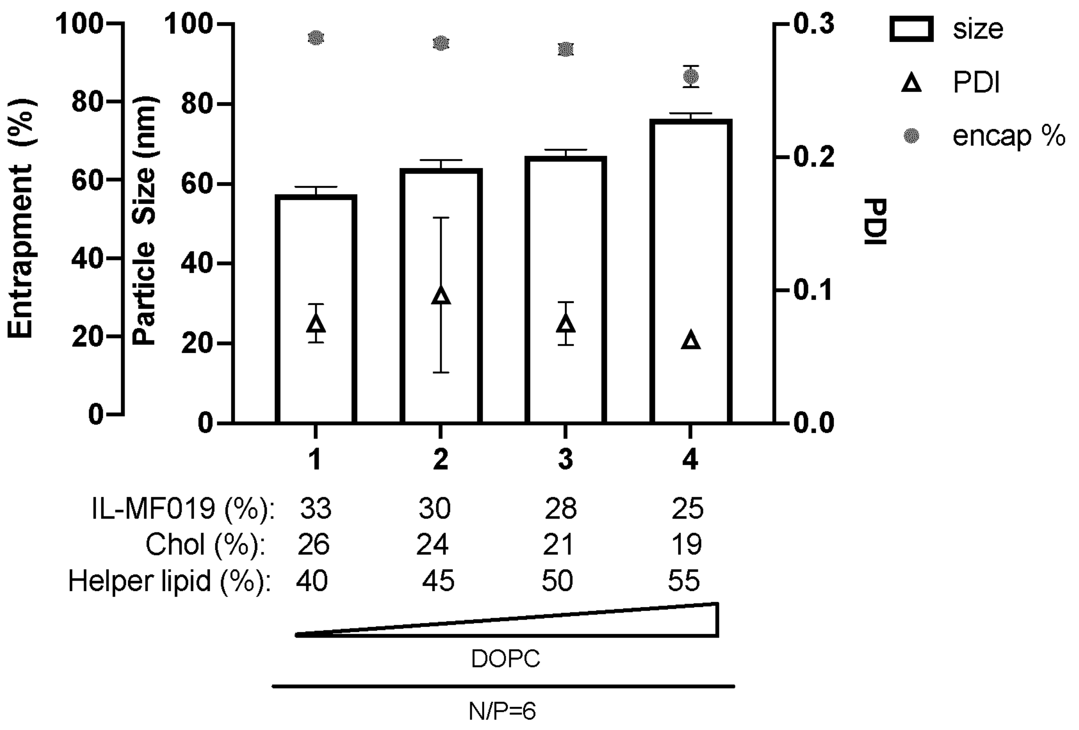
FIG. 1A shows entrapment %, particle size and polydispersity index (PDI) of lipid nanoparticles (top graph) containing a DNA vector encoding luciferase as a function of the amount of 1,2-dioleoyl-sn-glycero-3-phosphocholine (DOPC) neutral lipid (40-55 mol %). LNP formulations 1 to 4 comprise varying amounts of MF019 ionizable lipid, cholesterol and DOPC at the mol % indicated and PEG-DMG at 1 mol % at a nitrogen-to-phosphate ratio (N/P) of 6. Details of the lipid formulations are shown in Table 1.

Other objects, features, and advantages of the present invention will be apparent to one of skill in the art from the following detailed description and figures.

DETAILED DESCRIPTION

Neutral Lipid

In the context of the present disclosure, the term "neutral lipid" includes a lipid selected from sphingomyelin, a phosphatidylcholine lipid or mixtures thereof. The term "neutral lipid" is used interchangeably with the term "helper lipid" herein.

In some embodiments, the neutral lipid is selected from sphingomyelin, distearoylphosphatidylcholine (DSPC), dioleoylphosphatidylcholine (DOPC), 1-palmitoyl-2-oleoylphosphatidylcholine (POPC) and dipalmitoyl-phosphatidylcholine (DPPC). In certain embodiments, the neutral lipid is DOPC, DSPC or sphingomyelin. In one embodiment, the neutral lipid is DOPC. The neutral lipid content may include mixtures of two or more types of different neutral lipids. The neutral lipid content in some embodiments is greater than 20 mol %, greater than 25 mol %, greater than 30 mol %, greater than 32 mol %, greater than 34 mol %, greater than 36 mol %, greater than 38 mol %, greater than 40 mol %, greater than 42 mol %, greater than 44 mol %, greater than 46 mol %, greater than 48 mol % or greater than 50 mol %. In some embodiments, the upper limit of neutral lipid content is 70 mol %, 65 mol %, 60 mol %, 55 mol %, 50 mol % or 45 mol %. The disclosure also encompasses sub-ranges of any combination of the foregoing numerical upper and lower limits.

For example, in certain embodiments, the neutral lipid content is from 20 mol % to 60 mol % or 25 mol % to 60 mol % or 30 mol % to 60 mol % or 35 mol % to 60 mol % or 40 mol % to 60 mol % of total lipid present in the lipid nanoparticle.

The sphingomyelin content of the lipid nanoparticle in some embodiments is greater than 20 mol %, greater than 25 mol %, greater than 30 mol %, greater than 32 mol %, greater than 34 mol %, greater than 36 mol %, greater than 38 mol %, greater than 40 mol %, greater than 42 mol %, greater than 44 mol %, greater than 46 mol %, greater than 48 mol % or greater than 50 mol %. In some embodiments, the upper limit of sphingomyelin content is 70 mol %, 65 mol %, 60 mol %, 55 mol %, 50 mol % or 45 mol %. The disclosure also encompasses sub-ranges of any combination of the foregoing numerical upper and lower limits.

For example, in certain embodiments, the sphingomyelin content is from 20 mol % to 60 mol % or 25 mol % to 60 mol % or 30 mol % to 60 mol % or 35 mol % to 60 mol % or 40 mol % to 60 mol % of total lipid present in the lipid nanoparticle.

The phosphatidylcholine content of the lipid nanoparticle in some embodiments is greater than 20 mol %, greater than 25 mol %, greater than 30 mol %, greater than 32 mol %, greater than 34 mol %, greater than 36 mol %, greater than 38 mol %, greater than 40 mol %, greater than 42 mol %, greater than 44 mol %, greater than 46 mol %, greater than 48 mol % or greater than 50 mol %. In some embodiments, the upper limit of phosphatidylcholine content is 70 mol %, 65 mol %, 60 mol %, 55 mol %, 50 mol % or 45 mol %. The disclosure also encompasses sub-ranges of any combination of the foregoing numerical upper and lower limits.

For example, in certain embodiments, the phosphatidylcholine content is from 20 mol % to 60 mol % or 25 mol % to 60 mol % or 30 mol % to 60 mol % or 35 mol % to 60 mol % or 40 mol % to 60 mol % of total lipid present in the lipid nanoparticle.

The distearoylphosphatidylcholine (DSPC) content of the lipid nanoparticle in some embodiments is greater than 20 mol %, greater than 25 mol %, greater than 30 mol %, greater than 32 mol %, greater than 34 mol %, greater than 36 mol %, greater than 38 mol %, greater than 40 mol %, greater than 42 mol %, greater than 44 mol %, greater than 46 mol %, greater than 48 mol % or greater than 50 mol %. In some embodiments, the upper limit of distearoylphosphatidylcholine content is 70 mol %, 65 mol %, 60 mol %, 55 mol %, 50 mol % or 45 mol %. The disclosure also encompasses sub-ranges of any combination of the foregoing numerical upper and lower limits.

For example, in certain embodiments, the DSPC content is from 20 mol % to 60 mol % or 25 mol % to 60 mol % or 30 mol % to 60 mol % or 35 mol % to 60 mol % or 40 mol % to 60 mol % of total lipid present in the lipid nanoparticle.

The neutral lipid content is determined based on the total amount of lipid in the lipid nanoparticle, including the sterol.

Encapsulated DNA Vector

The lipid nanoparticle described herein comprises encapsulated DNA vector. As used herein, the term "DNA vector" refers to a polynucleotide that encodes at least one peptide, polypeptide or protein and that is either circular or has been linearized.

As used herein, the term "encapsulation," with reference to incorporating the DNA vector within a nanoparticle refers to any association of the DNA vector with any component or compartment of the lipid nanoparticle. In one embodiment, the DNA vector is incorporated in the electron dense region of a core of the lipid nanoparticle. In another embodiment, the DNA vector is incorporated between two closely apposed layers of lipid.

The DNA vector may replicate autonomously, or it may replicate by being inserted into the genome of the host cell, by methods well known in the art. Vectors that replicate autonomously will have an origin of replication or autonomous replicating sequence (ARS) that is functional in in a host cell. The DNA vector is usable in more than one host cell, e.g., in *E. coli* for cloning and construction, and in a mammalian cell for expression.

The DNA vectors may be administered to a subject for the purpose of repairing, enhancing or blocking or reducing the expression of a cellular protein or peptide. Accordingly, the nucleotide polymers can be nucleotide sequences including genomic DNA, cDNA, or RNA.

As will be appreciated by those of skill in the art, the vectors may encode promoter regions, operator regions or structural regions. The DNA vectors may contain double-stranded DNA or may be composed of a DNA-RNA hybrid. Non-limiting examples of double-stranded DNA include structural genes, genes including operator control and termination regions, and self-replicating systems such as vector DNA.

Single-stranded nucleic acids include antisense oligonucleotides (complementary to DNA and RNA), ribozymes and triplex-forming oligonucleotides. In order to have prolonged activity, the single-stranded nucleic acids will preferably have some or all of the nucleotide linkages substituted with stable, non-phosphodiester linkages, including, for example, phosphorothioate, phosphorodithioate, phophoroselenate, or O-alkyl phosphotriester linkages.

The DNA vectors may include nucleic acid in which modifications have been made in one or more sugar moieties and/or in one or more of the pyrimidine or purine bases. Such sugar modifications may include replacement of one or more hydroxyl groups with halogens, alkyl groups, amines, azido groups or functionalized as ethers or esters. In another embodiment, the entire sugar may be replaced with sterically and electronically similar structures, including aza-sugars and carbocyclic sugar analogs. Modifications in the purine or pyrimidine base moiety include, for example, alkylated purines and pyrimidines, acylated purines or pyrimidines, or other heterocyclic substitutes known to those of skill in the art.

The DNA vector may be modified in certain embodiments with a modifier molecule such as a peptide, protein, steroid or sugar moiety. Modification of a DNA vector with such molecule may facilitate delivery to a target site of interest. In some embodiments, such modification translocates the DNA vector across a nucleus of a target cell. By way of example, a modifier may be able to bind to a specific part of the DNA vector (typically not encoding of the gene-of-interest), but also has a peptide or other modifier that has nucleus-homing effects, such as a nuclear localization signal. A non-limiting example of a modifier is a steroid-peptide nucleic acid conjugate as described by Rebuffat et al., 2002, Faseb J. 16(11):1426-8, which is incorporated herein by reference. The DNA vector may contain sequences encoding different proteins or peptides. Promoter, enhancer, stress or chemically-regulated promoters, antibiotic-sensitive or nutrient-sensitive regions, as well as therapeutic protein encoding sequences, may be included as required. Non-encoding sequences may be present as well in the DNA vector.

The nucleic acids used in the present method can be isolated from natural sources, obtained from such sources as ATCC or GenBank libraries or prepared by synthetic methods. Synthetic nucleic acids can be prepared by a variety of solution or solid phase methods. Generally, solid phase synthesis is preferred. Detailed descriptions of the procedures for solid phase synthesis of nucleic acids by phosphite-triester, phosphotriester, and H-phosphonate chemistries are widely available.

In one embodiment, the DNA vector is double stranded DNA and comprises more than 700 base pairs, more than 800 base pairs or more than 900 base pairs or more than 1000 base pairs.

In another embodiment, the DNA vector is a nanoplasmid or a minicircle.

The DNA vector may be part of a CRISPR/Cas9 or zinc finger nuclease gene editing system. In another embodiment, the DNA vector is used in a diagnostic application.

Cationic Lipid

The term "cationic lipid" refers to any of a number of lipid species that carry a net positive charge at a selected pH. It should be understood that a wide variety of ionizable lipids can be used in the practice of the disclosure. For example, the cationic lipid may be an ionizable lipid that has a pKa such that the lipid is substantially neutral at physiological pH (e.g., pH of about 7.0) and substantially charged at a pH below its pKa. The pKa of the ionizable lipid may be less than 7.5, or more typically less than 7.0. In some cases, the cationic lipids comprise a protonatable tertiary amine (e.g., pH titratable) head group, C16 to C18 alkyl chains, a linker region (e.g., ester or ether linkages) between the head group and alkyl chains, and 0 to 3 double bonds. Such lipids include, but are not limited to ionizable lipids, such as DLin-KC2-CMA (KC2), DLin-MC3-DMA (MC3), nor-KC2 described in PCT/CA2022/050853 filed on May 26, 2022, nor-MC3 described in PCT/CA2022/050856 filed on May 26, 2022 and MF019 described in PCT/CA2022/050042 filed on Jan. 12, 2022 (each incorporated herein by reference). Other cationic lipids that may be used in embodiments of the disclosure include DODMA, DODAC, DOTMA, DDAB, DOTAP among other cationic lipids described in co-pending and commonly owned PCT/CA2022/050835 filed on May 26, 2022 titled "Method for Producing an Ionizable Lipid", which is incorporated herein by reference.

The cationic lipid content may be less than 60 mol %, less than 55 mol %, less than 50 mol, less than 45 mol %, less than 40 mol %, less than 35 mol %, less than 30 mol %, less than 25 mol %, less than 20 mol %, less than 15 mol %, less than 10 mol % or less than 5 mol %.

In certain embodiments, the cationic lipid content is from 5 mol % to 60 mol % or 10 mol % to 55 mol % or 10 mol % to 50 mol % or 15 mol % to 45 mol % or 20 mol % to 40 mol % of total lipid present in the lipid nanoparticle.

In one embodiment, the cationic lipid has a cLogP of at least 10, 10.5, 11.0 or 11.5.

In one embodiment, the amine-to-phosphate charge ratio (N/P) of the lipid nanoparticle is between 3 and 15, between 5 and 10, between 6 and 9, between 8 and 10 or between 5 and 8.

In some embodiments, the cationic lipid has one of the following Markush structures represented by Formula A, Formula B or Formula C below:

Formula A

A

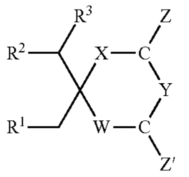

wherein each $R^1$ and $R^2$ group is, independently, a linear or branched alkyl group having from 4 to 30 carbon atoms, and wherein the alkyl groups may incorporate (i) from 0 to 4 heteroatoms, such as sulfur or oxygen atoms, (ii) from 0 to 5 C═C double bonds of E or Z geometry, and/or (iii) substituents such as OH, O-alkyl, S-alkyl, and $N(alkyl)_2$ bonded to a carbon atom, (iv) alkyl substituent having less than 5 carbon atoms, such as linear or branched substituents, including moieties selected from methyl, ethyl, propyl, isopropyl, butyl, isobutyl, and tert-butyl. $R^3$ may be H or a linear or branched alkyl group having from 4 to 30 carbon atoms, that may incorporate (i) from 0 to 4 heteroatoms, such as sulfur or oxygen atoms, (ii) from 0 to 5 C═C double bonds of E or Z geometry, and/or (iii) substituents such as OH, O-alkyl, S-alkyl, and $N(alkyl)_2$ bonded to a carbon atom, (iv) alkyl substituent having less than 5 carbon atoms, such as linear or branched substituents, including moieties selected from methyl, ethyl, propyl, isopropyl, butyl, isobutyl, and tert-butyl.

W and X are each, independently O or S;

Y is absent (the two C's are directly connected), or if Y is present is selected from:

(i) a metheno ($C_1$) bridge optionally substituted with a short alkylamino group of the type $[(CH_2)_n—NG^1G^2]$, wherein n=1-5 and $G^1$ and $G^2$ are, independently, a small alkyl having less than 5 carbon atoms (e.g., methyl, ethyl, propyl, isopropyl, butyl, isobutyl, and tert-butyl), or portions of a 4-7-membered ring containing N, so that $NG^1G^2$ is a nitrogen heterocycle moiety such as a 1-azetidinyl, 1-pyrrolidinyl, 1-piperidinyl, 1-azepanyl, 1-morpholinyl, 1-thiomorpholinyl, 1-piperazinyl; or (ii) an etheno ($C_2$) bridge optionally substituted with a short alkylamino group as specified above for the metheno case;

Z and Z' are, independently, H, or a short alkylamino group as stated above for the metheno case.

In one embodiment, the lipid of Formula A is the nor-KC2 lipid described herein.

Formula B

B

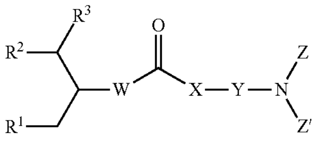

wherein each $R^1$ and $R^2$ group is, independently, a linear or branched alkyl group having from 4 to 30 carbon atoms, and wherein the alkyl groups may incorporate (i) from 0 to 4 heteroatoms, such as sulfur or oxygen atoms, (ii) from 0 to 5 C═C double bonds of E or Z geometry, and/or (iii) substituents such as OH, O-alkyl, S-alkyl, and $N(alkyl)_2$ bonded to a carbon atom, (iv) alkyl substituent having less than 5 carbon atoms, such as linear or branched substituents, including moieties selected from methyl, ethyl, propyl, isopropyl, butyl, isobutyl, and tert-butyl. $R^3$ may be H or a linear or branched alkyl group having from 4 to 30 carbon atoms, that may incorporate (i) from 0 to 4 heteroatoms, such as sulfur or oxygen atoms, (ii) from 0 to 5 C═C double bonds of E or Z geometry, and/or (iii) substituents such as OH, O-alkyl, S-alkyl, and $N(alkyl)_2$ bonded to a carbon atom, (iv) alkyl substituent having less than 5 carbon atoms, such as linear or branched substituents, including moieties selected from methyl, ethyl, propyl, isopropyl, butyl, isobutyl, and tert-butyl.

W is NH, or

N-small alkyl, such as $N—CH_3$, or

O

X is NH, or

N-small alkyl such as $N—CH_3$, or

O, or $CG^1G^2$, wherein $G^1$ and $G^2$ are, independently, H or the short-chain alkyl substituent;

Y is a short linear chain of 1-5 carbon atoms, and optionally substituted at one or more positions with the short-chain alkyl substituent;

Z and Z' are independently the short-chain alkyl substituent, or portions of a 4-7-membered ring containing N, so that NZZ' is a nitrogen heterocycle residue such as a 1-azetidinyl, 1-pyrrolidinyl, 1-piperidinyl, 1-azepanyl, 1-morpholinyl, 1-thiomorpholinyl, I-piperazinyl.

Cationic lipids, including but not limited to MF019 described herein, may be represented by Formula C having the structure below:

C

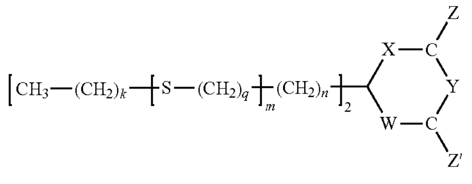

k may be 1-8, m may be 1-8, n may independently be 1 to 8, q may independently be 1 to 8, W and X are each, independently O or S;

Y is absent (the two C atoms are directly connected), or if Y is present is selected from;

(i) a metheno (C1) bridge optionally substituted with a short alkylamino group of the type $[(CH_2)_n\text{-}NG^1G^2]$, wherein n=1-5 and $G^1$ and $G^2$ are, independently, a small alkyl having less than 5 carbon atoms (e.g., methyl, ethyl, propyl, isopropyl, butyl, isobutyl, and tert-butyl), or portions of a 4-7-membered ring containing N, so that NG $G^2$ is a nitrogen heterocycle moiety such as a 1-azetidinyl, 1-pyrrolidinyl, 1-piperidinyl, 1-azepanyl, 1-morpholinyl, 1-thiomorpholinyl, 1-piperazinyl; or (ii) an etheno (C2) bridge optionally substituted with a short alkylamino group as specified above for the metheno case;

Z and Z' are, independently, H, or a short alkylamino group as stated above for the metheno case.

MF019 has the structure below:

MF019

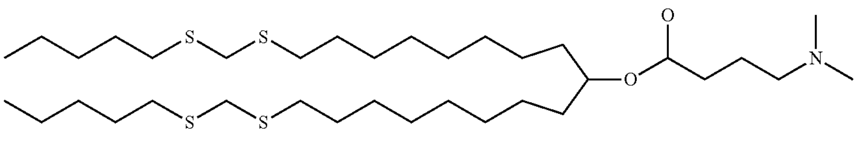

Additional sulfur-containing ionizable lipids that may be used in the practice of the disclosure include those described in commonly owned U.S. Ser. No. 63/340,687 filed on May 11, 2022, which is incorporated herein by reference.

Sterol

Examples of sterols include cholesterol, or a sterol derivative. Examples of derivatives include β-sitosterol, 3-sitosterol, campesterol, stigmasterol, fucosterol, or stigmastanol, dihydrocholesterol, ent-cholesterol, epi-cholesterol, desmosterol, cholestanol, cholestanone, cholestenone, cholesteryl-2'-hydroxyethyl ether, cholesteryl-4'-hydroxybutyl ether, 3β[N—(N'N'-dimethylaminoethyl)carbamoyl cholesterol (DC-Chol), 24(S)-hydroxycholesterol, 25-hydroxycholesterol, 25(R)-27-hydroxycholesterol, 22-oxacholesterol, 23-oxacholesterol, 24-oxacholesterol, cycloartenol, 22-ketosterol, 20-hydroxysterol, 7-hydroxycholesterol, 19-hydroxycholesterol, 22-hydroxycholesterol, 25-hydroxycholesterol, 7-dehydrocholesterol, 5α-cholest-7-en-3β-ol, 3,6,9-trioxaoctan-1-ol-cholesteryl-3e-ol, dehydroergosterol, dehydroepiandrosterone, lanosterol, dihydrolanosterol, lanostenol, lumisterol, sitocalciferol, calcipotriol, coprostanol, cholecalciferol, lupeol, ergocalciferol, 22-dihydroegocalciferol, ergosterol, brassicasterol, tomatidine, tomatine, ursolic acid, cholic acid, chenodeoxycholic acid, zymosterol, diosgenin, fucosterol, fecosterol or a salt or ester thereof.

In one embodiment, the sterol is present at from 15 mol % to 50 mol %, 18 mol % to 45 mol %, 20 mol % to 45 mol %, 25 mol % to 45 mol % or 30 mol % to 45 mol % based on the total lipid present in the lipid nanoparticle.

In another embodiment, the sterol is cholesterol and is present at from 15 mol % to 50 mol %, 18 mol % to 45 mol %, 20 mol % to 45 mol %, 25 mol % to 45 mol % or 30 mol % to 45 mol % based on the total lipid present in the lipid nanoparticle.

In one embodiment, the combined (i) sterol content (e.g., cholesterol or cholesterol derivative thereof); and (ii) neutral lipid content is at least 50 mol %; at least 55 mol %, at least 60 mol %, at least 65 mol %, at least 70 mol %, at least 75 mol %, at least 80 mol % or at least 85 mol % based on the total lipid present in the lipid nanoparticle.

Hydrophilic Polymer-Lipid Conjugate

In one embodiment, the lipid nanoparticle comprises a hydrophilic-polymer lipid conjugate capable of incorporation into the particle. The conjugate includes a vesicle-forming lipid having a polar head group, and (ii) covalently attached to the head group, a polymer chain that is hydrophilic. Example of hydrophilic polymers include polyethyleneglycol (PEG), polyvinylpyrrolidone, polyvinylmethylether, polyhydroxypropyl methacrylate, polyhydroxypropylmethacrylamide, polyhydroxyethyl acrylate, polymethacrylamide, polydimethylacrylamide, polymethyloxazoline, polyethyloxazoline, polyhydroxyethyloxazoline, polyhydroxypropyloxazoline, polysarcosine and polyaspartamide. In one embodiment, the hydrophilic-polymer lipid conjugate is a PEG-lipid conjugate. The hydrophilic polymer lipid conjugate may also be a naturally-occurring or synthesized oligosaccharide-containing molecule, such as monosialoganglioside (Gun). The ability of a given hydrophilic-polymer lipid conjugate to enhance the circulation longevity of the LNPs herein could be readily determined by those of skill in the art using known methodologies.

The hydrophilic polymer lipid conjugate may be present in the nanoparticle at 0.5 mol % to 5 mol %, or at 0.5 mol % to 3 mol %, or at 0.5 mol % to 2.5 mol % or at 0.5 mol % to 2.0 mol % or at 0.5 mol % to 1.8 mol % of total lipid. In certain embodiments, the hydrophilic polymer lipid conjugate may be present in the nanoparticle at 0 mol % to 5 mol %, or at 0 mol % to 3 mol %, or at 0 mol % to 2.5 mol % or at 0 mol % to 2.0 mol % or at 0 mol % to 1.8 mol % of total lipid.

In another embodiment, the PEG-lipid conjugate is present in the nanoparticle at 0.5 mol % to 5 mol %, or at 0.5 mol % to 3 mol % or at 0.5 mol % to 2.5 mol % or at 0.5 mol % to 2.0 mol % or at 0.5 mol % to 1.8 mol % of total lipid. In certain embodiments, the PEG-lipid conjugate may be present in the nanoparticle at 0 mol % to 5 mol %, or at 0 mol % to 3 mol %, or at 0 mol % to 2.5 mol % or at 0 mol % to 2.0 mol % or at 0 mol % to 1.8 mol % of total lipid.

Nanoparticle Preparation and Morphology

Delivery vehicles incorporating the DNA vector and having a core comprising an electron dense region and an aqueous portion surrounded at least partially by a lipid layer comprising at least a bilayer can be prepared using a variety of suitable methods, such as a rapid mixing/ethanol dilution process. Examples of preparation methods are described in Jeffs, L. B., et al., Pharm Res, 2005, 22(3):362-72; and Leung, A. K., et al., The Journal of Physical Chemistry. C, Nanomaterials and Interfaces, 2012, 116(34): 18440-18450, each of which is incorporated herein by reference in its entirety.

Without being bound by theory, the mechanism whereby a lipid nanoparticle comprising encapsulated DNA vector can be formed using the rapid mixing/ethanol dilution process can be hypothesized as beginning with formation of a dense region of hydrophobic vector nucleic acid-ionizable lipid core at pH 4 surrounded by a monolayer of neutral lipid/cholesterol that fuses with smaller empty vesicles as the pH is raised due to the conversion of the ionizable cationic lipid to the neutral form. As the proportion of bilayer neutral lipid increases, the bilayer lipid progressively forms bilayer protrusions and the ionizable lipid migrates to the interior hydrophobic core. At high enough neutral lipid contents, the exterior bilayer preferring neutral lipid can form a complete bilayer around the interior trapped volume.

By the term "core", it is meant a trapped volume of the nanoparticle that comprises an aqueous portion and an electron dense region. The aqueous portion and electron dense region can be visualized by cryo-EM microscopy. The electron dense region within the core is either only partially surrounded by the aqueous portion within the enclosed space or optionally entirely surrounded or enveloped by the aqueous portion within the core. For example, a portion of a periphery of the electron dense region within the core may be contiguous with the lipid layer of the lipid nanoparticle. For example, qualitatively, generally around 10-70% or 10-50% of the periphery of the electron dense region may be visualized as contiguous with a portion of the lipid layer of the lipid nanoparticle by cryo-EM microscopy.

In one embodiment, at least one about fifth of the core (trapped volume) contains the aqueous portion, and in which the electron dense core is either partially contiguous with the lipid layer comprising the bilayer or detached therefrom, as determined qualitatively by cryo-EM. In another embodiment, at least one about quarter of the core contains the aqueous portion, and in which the electron dense core is either partially contiguous with the lipid layer comprising the bilayer or detached therefrom, as determined qualitatively by cryo-EM. In a further embodiment, at least one about one third of the core contains the aqueous portion, and in which the electron dense core is either partially contiguous with the lipid layer comprising the bilayer or detached therefrom, as determined qualitatively by cryo-EM. In another embodiment, at least one about one half of the core contains the aqueous portion, and in which the electron dense core is either partially contiguous with the lipid layer comprising the bilayer or detached therefrom, as determined qualitatively by cryo-EM.

In one embodiment, the electron dense region is generally spherical in shape. In another embodiment, the electron dense region is hydrophobic.

The lipid nanoparticles herein may exhibit particularly high trapping efficiencies of DNA vector. Thus, in one embodiment, the trapping efficiency is at least 60, 65, 70, 75, 80, 85 or 90%.

In one embodiment, the DNA vector is at least partially encapsulated in the electron dense region. For example, in one embodiment, at least 50, 60, 70 or 80 mol % of the DNA vector is encapsulated in the electron dense region. In another embodiment, at least 50, 60, 70 or 80 mol % of the ionizable lipid is in the electron dense region.

In another embodiment, the DNA vector and cationic lipid are present in the electron dense region. In one embodiment, this morphology provides surprising improvements in stability of the encapsulated cargo after administration to a subject. In a further embodiment, the neutral lipid is present in the lipid layer comprising the bilayer.

The lipid nanoparticle may comprise a single bilayer or comprise multiple concentric lipid layers (i.e., multi-lamellar). The one or more lipid layers, including the bilayer, may form a continuous layer surrounding the core or may be discontinuous. The lipid layer may be a combination of a bilayer and a monolayer in some embodiments. In one embodiment, the lipid layer is a continuous bilayer that surrounds the core.

The lipid nanoparticle of the present disclosure possesses a unique morphology as visualized by cryo-EM. In one non-limiting example, as the neutral lipid content increases, the core assumes a morphology in which the electron dense region is surrounded and "floats" within the aqueous portion, which in turn is surrounded by the lipid bilayer (e.g., FIG. 9).

Thus, in certain embodiments the electron dense region of the core is separated from the lipid layer comprising the bilayer by the aqueous portion. For example, the disclosure provides a lipid nanoparticle preparation comprising a plurality of lipid nanoparticles in which at least 20%, 30%, 40%, 50%, 60% or 70% of the particles as determined by cryo-EM microscopy have a core with an electron dense region that is surrounded by the aqueous portion and in which the aqueous portion is surrounded by the lipid layer comprising the bilayer as visualized by cryo-EM microscopy.

The lipid nanoparticle of the present disclosure possesses a unique morphology as visualized by cryo-EM. In one non-limiting example, as the neutral lipid content increases, the core assumes a morphology in which the electron dense region is contiguous with the lipid bilayer (e.g., FIG. 9).

Thus, in certain embodiments, the disclosure provides a lipid nanoparticle preparation comprising a plurality of lipid nanoparticles in which at least 20%, 30%, 40%, 50%, 60% or 70% of the particles as determined by cryo-EM microscopy have a core with an electron dense region that is contiguous with the lipid layer comprising the bilayer as visualized by cryo-EM microscopy.

In another embodiment, and without being limiting, the disclosure provides a lipid nanoparticle preparation comprising a plurality of lipid nanoparticles in which generally at least 20%, 30%, 40%, 50%, 60% or 70% of the particles have a core comprising an electron dense region surrounded or enveloped by a continuous aqueous space disposed between the lipid layer (e.g., bilayer) and the electron dense region as visualized by cryo-EM microscopy.

Improved Gene Expression from DNA Vector In Vivo

As used herein, "expression" of a DNA vector refers to translation of an mRNA into a peptide (e.g., an antigen), polypeptide, or protein (e.g., an enzyme) and also can include the post-translational modification of the peptide, polypeptide or fully assembled protein (e.g., enzyme).

The morphology of the lipid nanoparticle may facilitate long circulation lifetimes thereof after administration to a patient, thereby improving DNA vector delivery to a wider range of tissues than previous formulations for DNA vector delivery, including but not limited to delivery to any disease site, such as a tumor, or in the liver, spleen, lung and/or bone marrow. Whether or not a lipid nanoparticle exhibits such enhanced delivery to a given tissue or organ can be determined by biodistribution studies in an in vivo mouse model using a lipid marker, such as DiD (DiIC18(5); 1,1'-dioctadecyl-3,3,3',3'-tetramethylindodicarbocyanine, 4-chlorobenzenesulfonate salt). In additional or alternative embodiments, green fluorescent protein (GFP) may be used to detect nucleic acid expression from the vector in a given tissue or organ and is carried out in an in vivo model, namely a mouse model. In particular, according to such embodiments, LNP DNA vector systems are prepared using DNA vector coding for GFP and biodistribution and GFP expression is evaluated using flow cytometry following systemic administration. As would be appreciated by those of skill in the art, other reporter systems besides GFP can be used to detect nucleic acid expression at a target site, such as luciferase.

In one embodiment, the lipid nanoparticle exhibits an increase in gene expression of at least 10% relative to an Onpattro™-type formulation as measured at least 12 or 48 hours post-administration. To assess whether a given lipid nanoparticle exhibits an increase in gene expression in a relevant cell, tissue or organ at any time point after 12 or 48 hours post-injection, the two formulations being compared are identical apart from the content of neutral lipid and are subjected to the same experimental methods and materials to determine in vivo expression. Expression of a reporter gene is measured as set forth in Example 4 (green fluorescent protein) and Example 5 (luciferase). The "Onpattro"-type formulation contains ionizable lipid/DSPC/cholesterol/PEG-lipid at 50/10/38.5/1.5; mol:mol and the ionizable lipid is the same as that in the lipid nanoparticle formulation being tested for increased expression.

In one embodiment, the lipid nanoparticle exhibits at least a 10%, 20%, 30%, 40%, 50%, 60%, 70%, 80%, 90%, 100%, 110%, 120%, 130%, 140%, 150%, 160%, 170%, 180%, 190% or 200% increase in gene expression in vivo in any disease site, such as a tumor, or in the liver, spleen, lung and/or bone marrow at any time point after 12 or 48 hours post-injection as compared to a lipid nanoparticle encapsulating DNA vector with an "Onpattro"-type formulation of ionizable lipid/DSPC/cholesterol/PEG-lipid at 50/10/38.5/1.5; mol:mol, wherein the gene expression is measured in an animal model by detection of an expression product of a suitable reporter gene, such as a green fluorescent protein (GFP) or luciferase (Luc).

In one embodiment, the lipid nanoparticle exhibits at least a 10%, 20%, 30%, 40%, 50%, 60%, 70%, 80%, 90%, 100%, 110%, 120%, 130%, 140%, 150%, 160%, 170%, 180%, 190% or 200% increase in gene expression in vivo in any disease site, such as a tumor, or in the liver, spleen, lung and/or bone marrow as measured at 12 hr, 24 hr, 48 hr, 3 days, 4 days, 5 days, 6 days, 7 days, 8 days, 9 days, 10 days, 11 days, 12 days, 13 days, 14 days or 15 days post-injection.

In one embodiment, the lipid nanoparticle exhibits at least a 10%, 20%, 30%, 40%, 50%, 60%, 70%, 80%, 90%, 100%, 110%, 120%, 130%, 140%, 150%, 160%, 170%, 180%, 190% or 200% increase in gene expression in vivo in any disease site, such as a tumor, or in the liver, spleen, lung and/or bone marrow at any time point between 24 hr and 30 days, 48 hr and 15 days or 3 days and 10 days post-injection.

The lipid nanoparticles comprising the DNA vector may be targeted to tissues, organs or other target sites that contain rapidly dividing or proliferating cells in adult or fetal cells. The lipid nanoparticles described herein may exhibit enhanced expression of an encoded protein or peptide at such disease sites. DNA vector encapsulated by the lipid nanoparticles herein may facilitate delivery to the cytosol and entry of the nucleic acid into the nucleus of a cell. Without intending to be limited by theory, entry of the DNA vector into the nucleus and expression of protein or peptide therein may be observed primarily in populations of cells that are rapidly dividing. Thus, the lipid nanoparticles encapsulating the DNA vector and having enhanced in vivo biodistribution and/or expression of the DNA vector in tissues and organs beyond the liver may be particularly advantageous for treatment of diseases or disorders that are characterized by rapidly dividing cells. The lipid nanoparticles of the present disclosure may also be particularly suitable for in utero administration to target rapidly dividing cells.

Such site in the body may be a disease site that is cancerous or the lipid nanoparticles may be targeted to the cardiovascular system in the case of a cardiovascular disease with rapidly dividing cells. In another embodiment, the lipid nanoparticles are targeted to sites having rapidly dividing cells in embryonic tissue or organs, such as cells undergoing differentiation. Targeting the lipid nanoparticles to such sites may provide for treatment or prevention of congenital disease in utero before birth. In a further embodiment, the lipid nanoparticles are targeted to bone marrow as such target site has cells that are rapidly dividing.

In one embodiment, the lipid nanoparticle exhibits at least a 10%, 20%, 30%, 40%, 50%, 60%, 70%, 80%, 90%, 100%, 110%, 120%, 130%, 140%, 150%, 160%, 170%, 180%, 190% or 200% increase in DNA expression in vivo in any disease site having rapidly dividing cells, such as a tumor, in a tumour-bearing mouse model relative to DNA expression in vivo in a non-tumour-bearing mouse model, in which the DNA expression product is measured in the blood for a secreted protein/peptide or a bodily site at 12 hr, 24 hr, 48 hr, 3 days, 4 days, 5 days, 6 days, 7 days, 8 days, 9 days, 10 days, 11 days, 12 days, 13 days, 14 days or 15 days post-injection.

In one embodiment, the cells at the target site are dividing at a rate that is at least 30% greater than surrounding parenchymal cells. The tissue is isolate, fixed and sectioned and the sections are then stained for the presence of markers of cells division, such as proteins specifically expressed during mitosis, cell cycle associated proteins or chromatin. Examples of techniques known to those of skill in the art are provided in Romar et al., 2016, Journal of Investigative Dermatology, 136(1):e1-e7, which is incorporated herein by reference. A particularly suitable method known to those of skill in the art is staining and microscopy of Ki-67.

In another embodiment, the lipid nanoparticles comprising the DNA vector are used in diagnostic applications. The DNA vector may localize in target cells (e.g., rapidly dividing cells) and expression of encoded DNA may be used to provide a measurable signal.

Pharmaceutical Formulations

In some embodiments, the lipid nanoparticle comprising the DNA vector is part of a pharmaceutical composition and is administered to treat and/or prevent a disease condition. The treatment may provide a prophylactic (preventive), ameliorative or a therapeutic benefit. The pharmaceutical composition will be administered at any suitable dosage.

In one embodiment, the pharmaceutical composition is administered parentally, i.e., intra-arterially, intravenously, subcutaneously or intramuscularly. In yet a further embodiment, the pharmaceutical compositions are for intra-tumoral or in-utero administration. In another embodiment, the pharmaceutical compositions are administered intranasally, intravitreally, subretinally, intrathecally or via other local routes.

The pharmaceutical composition comprises pharmaceutically acceptable salts and/or excipients.

The compositions described herein may be administered to a patient. The term patient as used herein includes a human or a non-human subject.

Method of Medical Treatment and Uses of the Lipid Nanoparticles

In one embodiment, there is provided a lipid nanoparticle as described in any embodiment herein for use to treat and/or prevent a condition or disease by producing a protein or polypeptide in vitro or in vivo, wherein the lipid nanoparticle comprises at least one DNA vector that encodes the protein or polypeptide. In one embodiment, the use comprises contacting a mammalian cell, tissue or organism with the lipid nanoparticle. In one embodiment, the mammalian cell is contacted in vitro or in vivo. In another embodiment, the mammalian cell is a rapidly dividing cell.

In one embodiment, there is provided a method to treat a mammalian cell by administering the lipid nanoparticle as described in any embodiment herein to treat and/or prevent a condition or disease by producing a protein or polypeptide in vitro or in vivo, wherein the formulation comprises at least one DNA vector that encodes the protein or polypeptide, and wherein the method comprises contacting the mammalian cell with the lipid nanoparticle. In one embodiment, the mammalian cell is contacted in vitro or in vivo.

In one embodiment, the mammalian cell is a cancer cell such as a lung cancer cell, colon cancer cell, rectal cancer cell, anal cancer cell, bile duct cancer cell, small intestine cancer cell, stomach (gastric) cancer cell, esophageal cancer cell, gallbladder cancer cell, liver cancer cell, pancreatic cancer cell, appendix cancer cell, breast cancer cell, ovarian cancer cell, cervical cancer cell, prostate cancer cell, renal cancer cell, a cancer cell of the central nervous system, a glioblastoma tumor cell, skin cancer cell, lymphoma cell, choriocarcinoma tumor cell, head and neck cancer cell, osteogenic sarcoma tumor cell, and blood cancer cell.

The lipid nanoparticles herein can be used to treat a wide variety of vertebrates, including mammals, such as, but not limited to, canines, felines, equines, bovines, ovines, caprines, rodents (e.g., mice, rats, and guinea pigs), lagomorphs, swine and primates (e.g., humans, monkeys and chimpanzees).

The examples are intended to illustrate the preparation of specific lipid nanoparticle DNA vector preparations and properties thereof but are in no way intended to limit the scope of the invention.

EXAMPLES

Materials

The lipid 1,2-distearoyl-sn-glycero-3-phosphorylcholine (DSPC), Egg sphingomyelin (ESM), 1,2-dimyristoyl-rac-glycero-3-methoxypolyethylene glycol-2000 (PEG-DMG), and 1,2-dioleoyl-sn-glycero-3-phosphocholine (DOPC) were purchased from Avanti Polar Lipids (Alabaster, AL). Cholesterol and 10× Phosphate Buffered Saline (pH 7.4) were purchased from Sigma Aldrich (St Louis, MO). The ionizable amino-lipid 2,2-dilinoleyl-4-(2-dimethylaminoethyl)-[1,3]-dioxolane (DLin-KC2-DMA) and MF019 were synthesized as previously described in PCT/CA2022/050835 titled "Method for Producing an Ionizable Lipid" filed on May 26, 2022, which is incorporated herein by reference. A DNA vector encoding luciferase was purchased from Aldevron™ (Fargo, NO). Steady-Glo™ Luciferase assay kit (Promega, Madison, WI) was used to analyse luciferase activity.

Methods

Preparation of Lipid Nanoparticles (LNP) Containing DNA Vector

Lipids used in the formulation, such as ionizable cationic lipids, neutral lipid, cholesterol, and PEG-DMG, were dissolved in ethanol at the appropriate ratios to a final concentration of 10 mM total lipid. Nucleic acid was dissolved in an appropriate buffer such as 25 mM sodium acetate pH 4 or sodium citrate pH 4 to a concentration necessary to achieve the appropriate amine-to-phosphate ratios. The aqueous and organic solutions were mixed using a rapid-mixing device as described in Kulkarni et al., 2018, ACS Nano, 12:4787 and Kulkarni et al., 2019, Nanoscale, 11:9023 (incorporated herein by reference) at a flow rate ratio of 3:1 (v/v; respectively) and a total flow rate of 20 mL/min. The resultant mixture was dialyzed directly against 1000-fold volume of PBS pH 7.4. All formulations were concentrated using an Amicon™ centrifugal filter unit and analysed using the methods described below.

Analysis of LNP

Particle size analysis of LNPs in PBS was carried out using backscatter measurements of dynamic light scattering with a Malvern Zetasizer™ (Worcestershire, UK). The reported particle sizes correspond to the number-weighted average diameters (nm). Total lipid concentrations were determined by extrapolation from the cholesterol content, which was measured using the Cholesterol E-Total Cholesterol Assay (Wako Diagnostics, Richmond, VA) as per manufacturer's recommendations. Encapsulation efficiency of the formulations was determined using the Quant-iT PicoGreen™ dsDNA Assay kit (Invitrogen™, Waltham, MA). Briefly, the total DNA content in solution was measured by lysing lipid nanoparticles in a solution of TE containing 2% Triton Tx-100, and free DNA vector in solution (external to LNP) was measured based on the PicoGreen fluorescence in a Tris-EDTA (TE) solution without Triton. Total DNA content in the formulation was determined using a modified Bligh-Dyer extraction procedure. Briefly, LNP-DNA vector formulations were dissolved in a mixture of chloroform, methanol, and PBS that results in a single phase and the absorbance at 260 nm measured using a spectrophotometer.

In Vitro Analysis in Huh7 Cells

Huh7 cells were cultured in Dulbecco's Modified Eagle Medium (DMEM) supplemented with 10% Fetal Bovine Serum (FBS). For cell treatments, 10,000 cells were added to each well in a 96-well plate. After 24 hours, the medium was aspirated and replaced with medium containing diluted LNP at the relevant concentration over a range of 0.03-10 μg/mL DNA vector. Expression analysis was performed 24 hours later, and luciferase levels measured using the Steady-Glo Luciferase™ kit. Cells were lysed using the Glo Lysis™ buffer.

Measurement of Fluorescence in Intact Organs Tissues In Vivo

LNPs comprising DNA vector encoding for luciferase and comprising DiD lipid marker at 0.75 mol % were used to assess in vivo biodistribution. The DNA vector LNPs were injected at a dose of 1 mg/kg of DNA intravenously (i.v.) in CD-1 mice at a volume using the formula weight of the mouse (in grams)*10 μL. At 24 hours post-injection, mice were anesthetized in 5% isofluorane (set to 1% air flow) followed by $CO_2$ to induce asphyxiation until the animals lost their reflexes. This was followed by cervical dislocation. The animals were subsequently imaged on an In Vivo Imaging System (IVIS™) manufactured by PerkinElmer™.

After imaging, the skin was cut from the bladder to the rib cage and the skin was pinned back without opening the peritoneum. The animals with the organs intact were imaged on the IVIS™ imager. Liver, spleen and lungs were removed from the abdominal cavity and placed on a plastic dish and imaged using the IVIS™ imager.

Tissue Homogenate Assay

Tissues were removed from the mice and placed in 2 mL tubes and snap frozen in liquid nitrogen. The tissues were subsequently frozen at −80° C. An appropriate volume of GLO™ lysis buffer from Promega™ was added to each of the tubes, ensuring that the samples remained frozen before addition of the lysis buffer. Samples were placed in a FastPrep™ homogenizer and the homogenizer was operated at a speed of "6" for 20 seconds and repeated 2 times for a total of three rounds. The homogenized samples were spun down for 10 minutes at 12,000 rpm at room temperature and subsequently 50 μL of homogenate in duplicate was added to a black plate. The plate was transferred to a plate reader and the fluorescence was read at 640 nm excitation/720 nm emissions. Luminescence was determined by adding 50 μL of Steady Glo™ substrate into the homogenate sample and a luciferase signal was read.

Secreted Protein In Vivo Expression Assay

The DNA vector LNPs were injected at a dose of 1 mg/kg intravenously (i.v.) in tumour and non-tumour bearing NSG strain number 005557 mice at a volume using the formula weight of the mouse (in grams)*5 μL. At −1, 2 and 5 days post-injection, post-injection, blood was drawn via saphenous vein blood and serum separated through centrifugation with SST tubes (BD Microtainer™ Tubes, BD Diagnostics™). Secreted reporter protein is measured in serum using an activity-based assay.

Example 1: Effect of Increasing DOPC Neutral Lipid Content on LNP Size, PDI, Encapsulation Efficiency and Transfection Efficiency LNP formulations containing the ionizable lipid MF019, neutral lipid DOPC, cholesterol, and 1 mol % PEG-DMG were prepared containing DNA vector encoding luciferase. The molar percentage of DOPC was increased from 40-55 mol %. Correspondingly, the ionizable lipid and cholesterol levels were decreased while maintaining a ratio of 1.3 mol/mol, respectively.

Figure 1B:
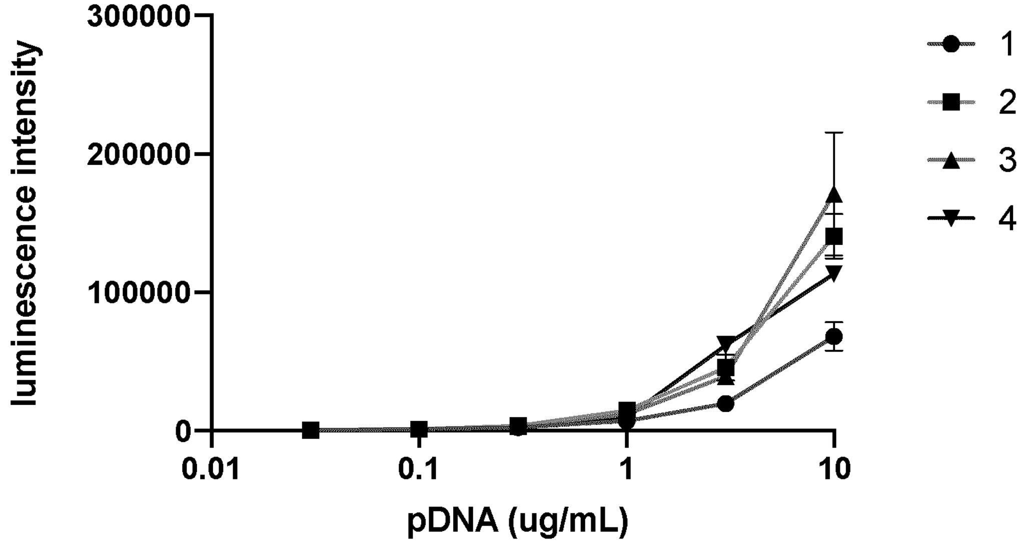
FIG. 1B shows luminescence intensity after addition of LNP formulations 1 to 4 to Huh7 cells over a range of 0.03-10 μg/mL DNA encoding luciferase. Details of the lipid formulations are shown in Table 1.
Figure 2A:
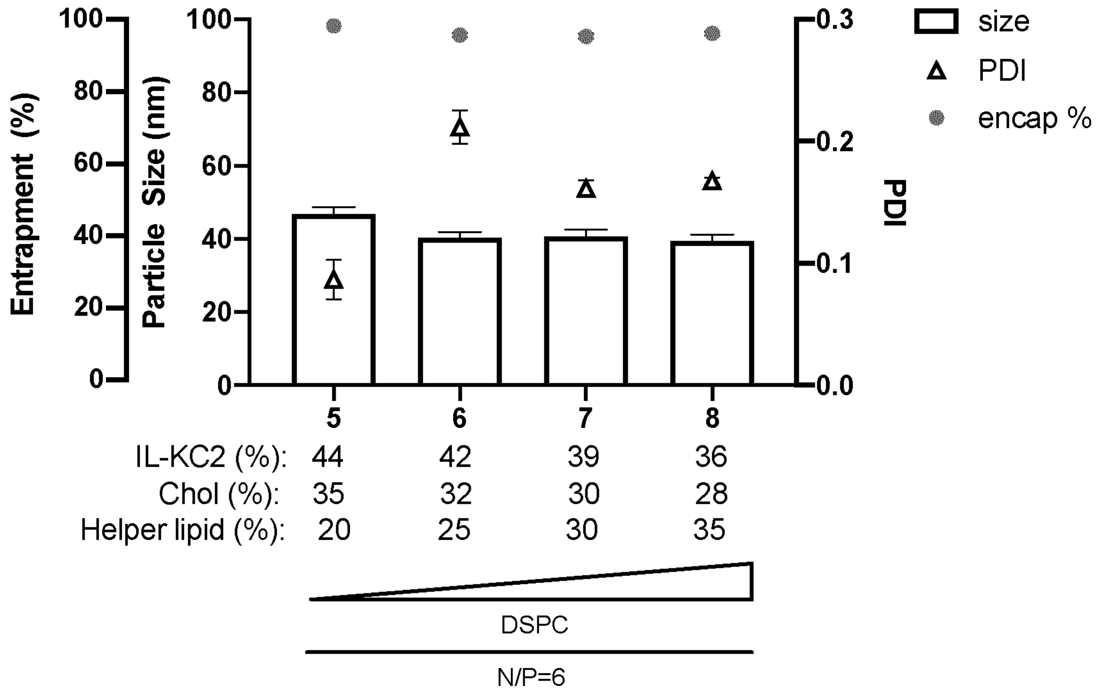
FIG. 2A shows entrapment %, particle size and PDI of lipid nanoparticles (top graph) containing a DNA vector encoding luciferase as a function of the amount of 1,2-distearoyl-sn-glycero-3-phosphocholine (DSPC) neutral lipid (20-35 mol %). LNP formulations 5 to 8 comprise varying amounts of DLin-KC2-DMA (KC2) ionizable lipid, cholesterol and DSPC at the mol % indicated and PEG-DMG at 1 mol % at an N/P of 6. Details of the lipid formulations are shown in Table 2.
Figure 2B:
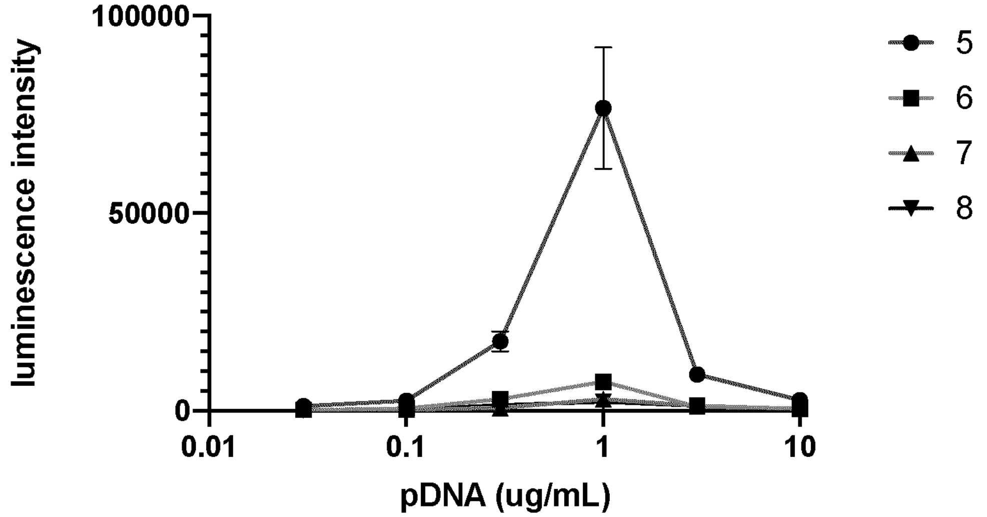
FIG. 2B shows luminescence intensity after addition of LNP formulations 5 to 8 to Huh7 cells over a range of 0.03-10 μg/mL DNA encoding luciferase. Details of the lipid formulations are shown in Table 2.
Figure 2C:
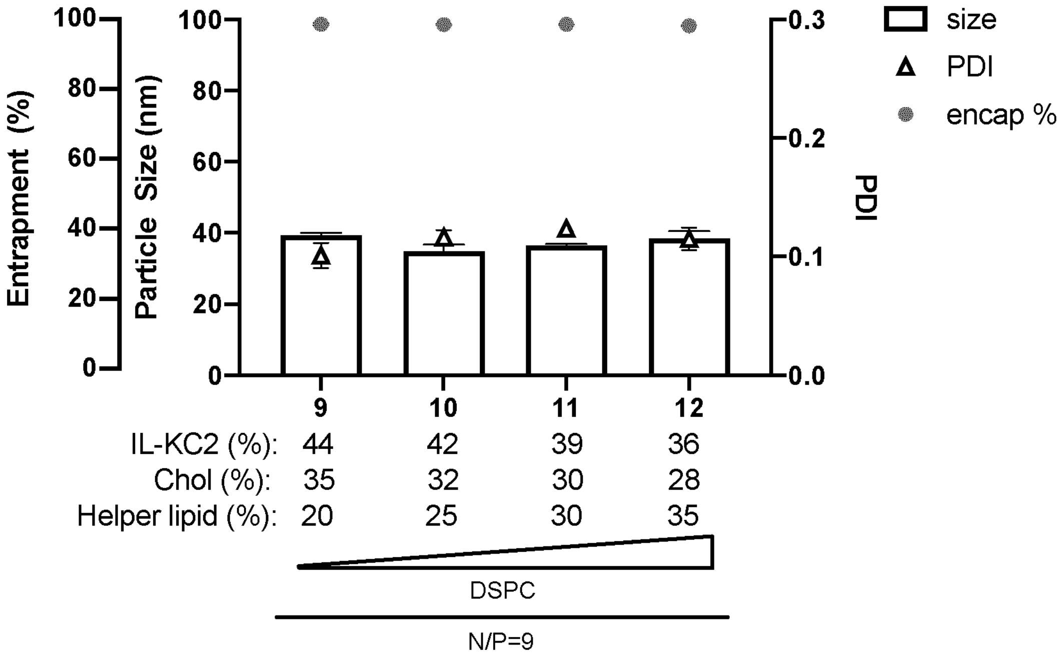
FIG. 2C shows entrapment %, particle size and PDI of lipid nanoparticles (top graph) containing a DNA vector encoding luciferase as a function of the amount of DSPC neutral lipid (20-35 mol %). LNP formulations 9 to 12 comprise varying amounts of KC2 ionizable lipid, cholesterol and DSPC at the mol % indicated and PEG-DMG at 1 mol % at an N/P of 9. Details of the lipid formulations are shown in Table 2.
Figure 2D:
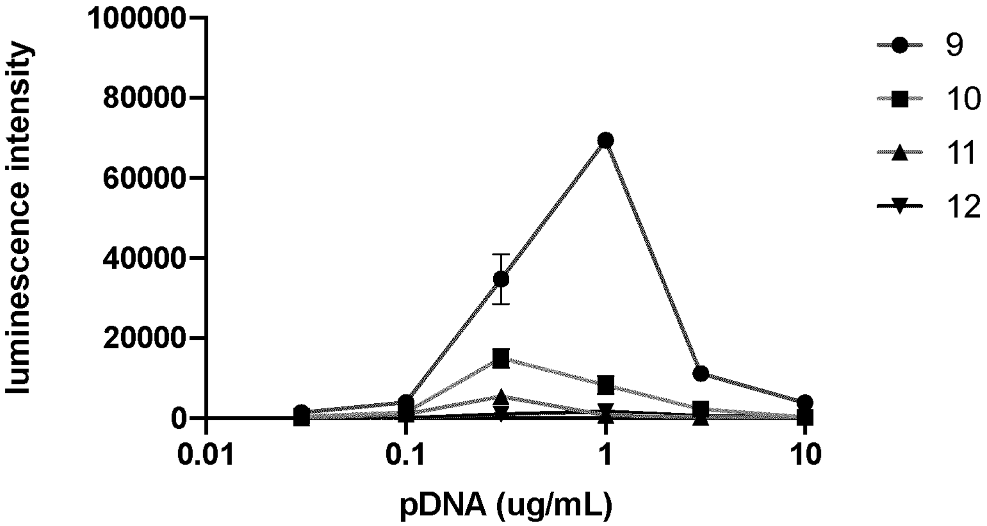
FIG. 2D shows luminescence intensity after addition of LNP formulations 9 to 12 to Huh7 cells over a range of 0.03-10 μg/mL DNA encoding luciferase. Details of the lipid formulations are shown in Table 2.
Figure 2E:
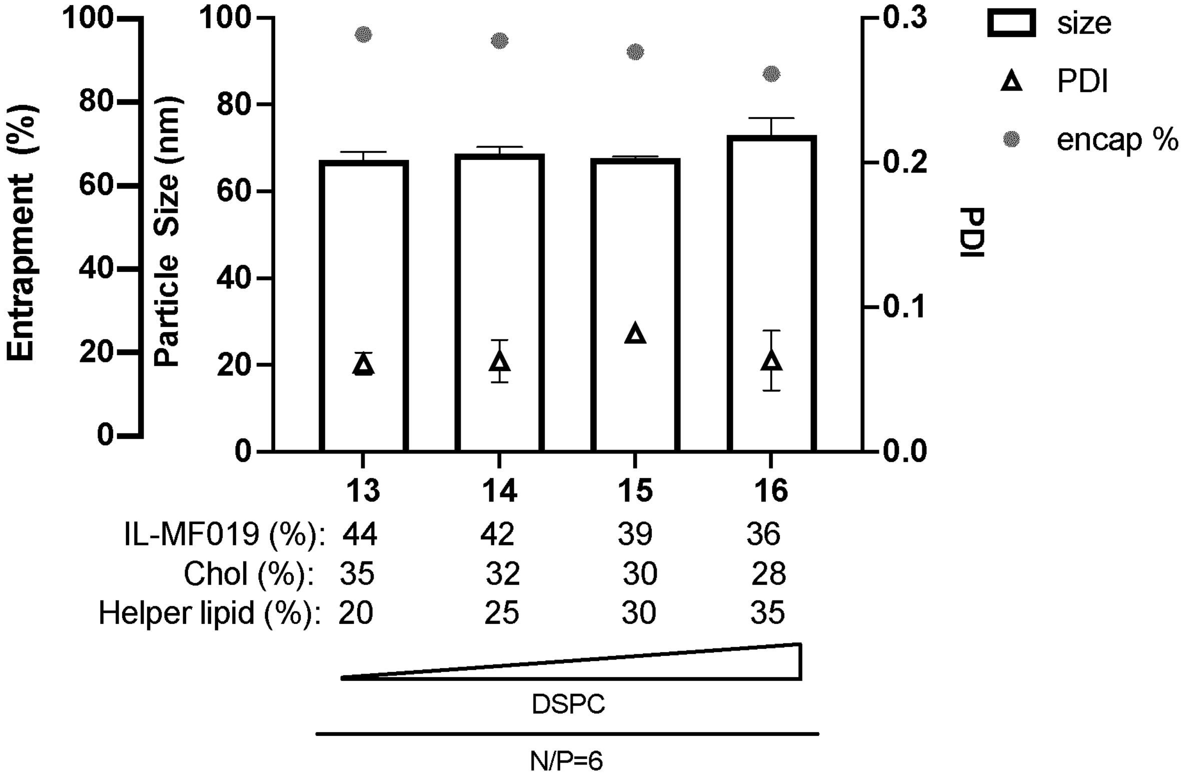
FIG. 2E shows entrapment %, particle size and PDI of lipid nanoparticles (top graph) containing a DNA vector encoding luciferase as a function of the amount of DSPC neutral lipid (20-35 mol %). LNP formulations 13 to 16 comprise varying amounts of MF019 ionizable lipid, cholesterol and DSPC at the mol % indicated and PEG-DMG at 1 mol % at an N/P of 6. Details of the lipid formulations are shown in Table 2.
Figure 2F:
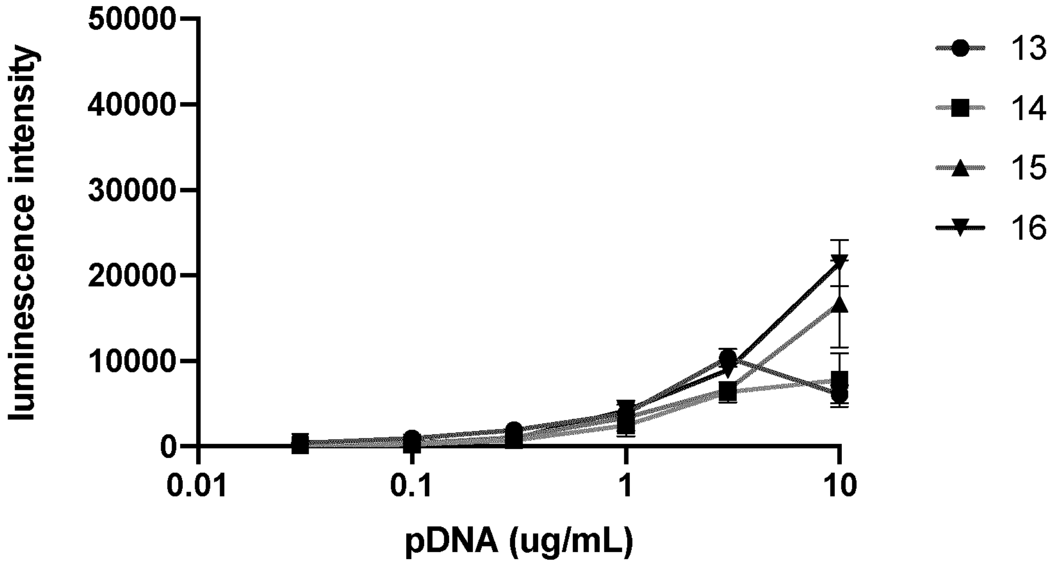
FIG. 2F shows luminescence intensity after addition of LNP formulations 13 to 16 to Huh7 cells over a range of 0.03-10 μg/mL DNA encoding luciferase. Details of the lipid formulations are shown in Table 2.
Figure 2G:
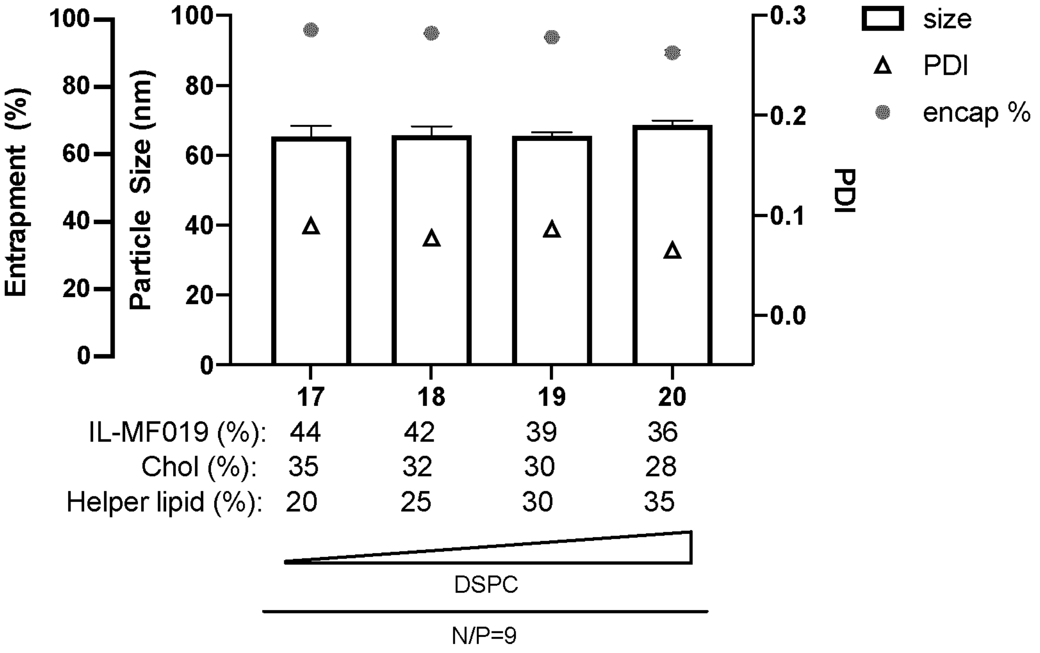
FIG. 2G shows entrapment %, particle size and PDI of lipid nanoparticles (top graph) containing a DNA vector encoding luciferase as a function of the amount of DSPC neutral lipid (20-35 mol %). LNP formulations 17 to 20 comprise varying amounts of MF019 ionizable lipid, cholesterol and DSPC at the mol % indicated and PEG-DMG at 1 mol % at an N/P of 9. Details of the lipid formulations are shown in Table 2.
Figure 2H:
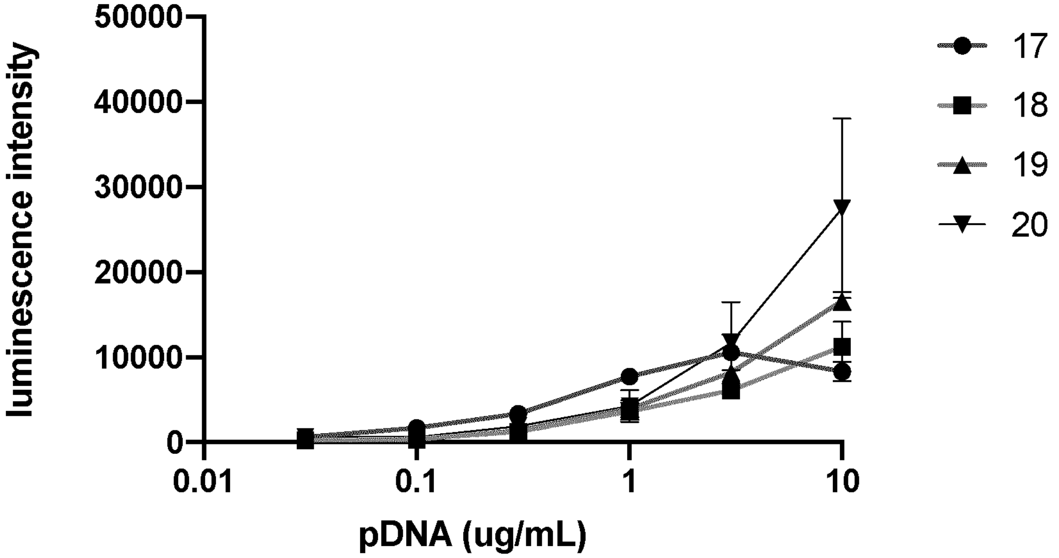
FIG. 2H shows luminescence intensity after addition of LNP formulations 17 to 20 to Huh7 cells over a range of 0.03-10 μg/mL DNA encoding luciferase. Details of the lipid formulations are shown in Table 2.
Figure 2I:
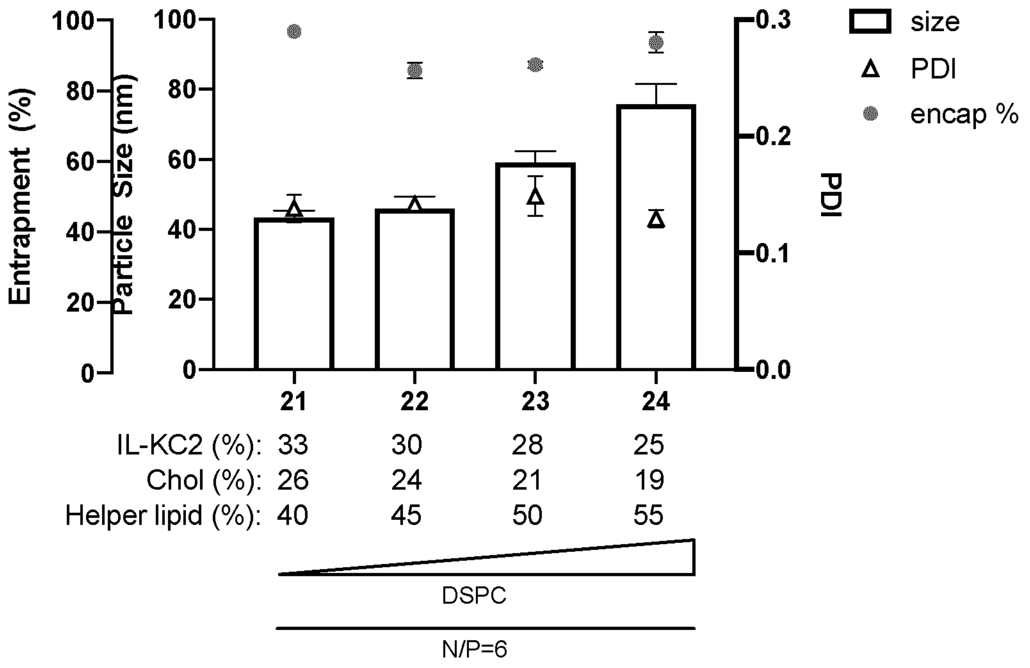
FIG. 2I shows entrapment %, particle size and PDI of lipid nanoparticles (top graph) containing a DNA vector encoding luciferase as a function of the amount of DSPC neutral lipid (40-55 mol %). LNP formulations 21 to 24 comprise varying amounts of KC2 ionizable lipid, cholesterol and DSPC at the mol % indicated and PEG-DMG at 1 mol % at an N/P of 6. Details of the lipid formulations are shown in Table 2.
Figure 2J:
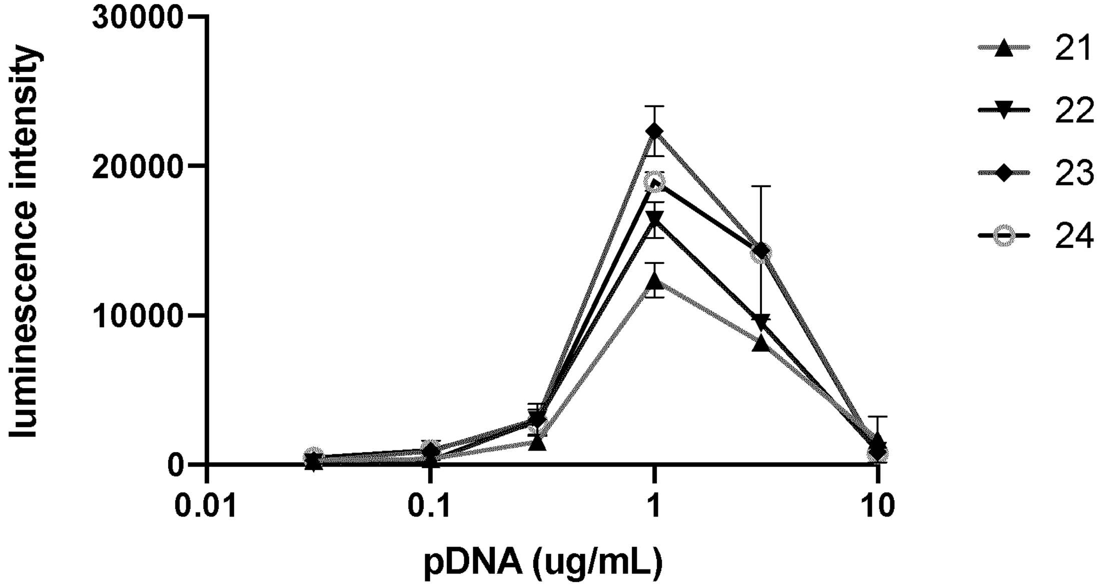
FIG. 2J shows luminescence intensity after addition of LNP formulations 21 to 24 to Huh7 cells over a range of 0.03-10 μg/mL DNA encoding luciferase.
Figure 2K:
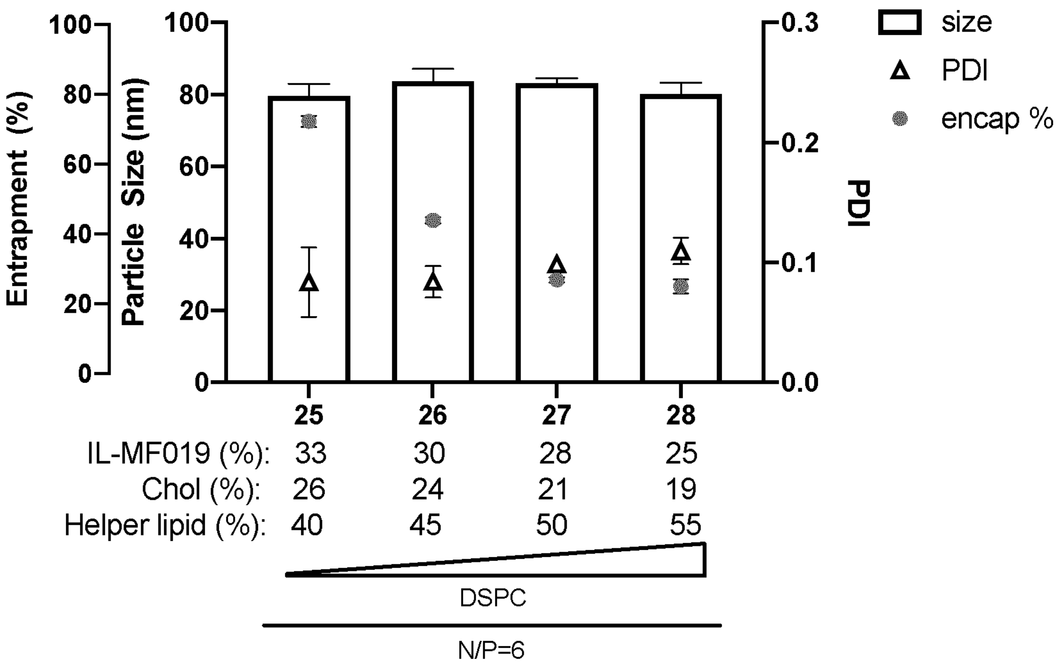
FIG. 2K shows entrapment %, particle size and PDI of lipid nanoparticles (top graph) containing a DNA vector encoding luciferase as a function of the amount of DSPC neutral lipid (40-55 mol %). LNP formulations 25 to 28 comprise varying amounts of MF019 ionizable lipid, cholesterol and DSPC at the mol % indicated and PEG-DMG at 1 mol % at an N/P of 6. Details of the lipid formulations are shown in Table 2.
Figure 2L:
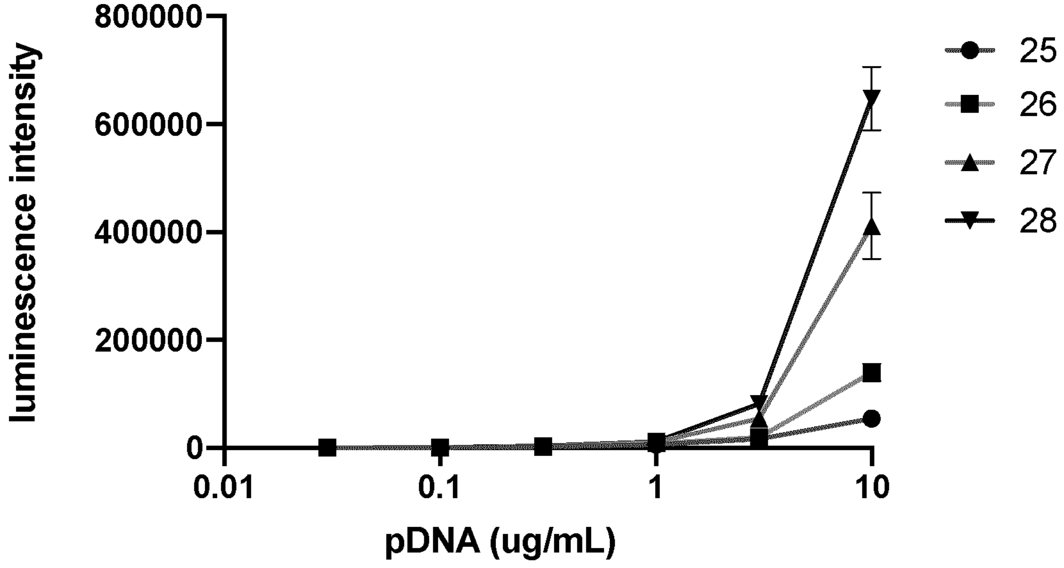
FIG. 2L shows luminescence intensity after addition of LNP formulations 25 to 28 to Huh7 cells over a range of 0.03-10 μg/mL DNA encoding luciferase. Details of the lipid formulations are shown in Table 2.
Figure 2M:
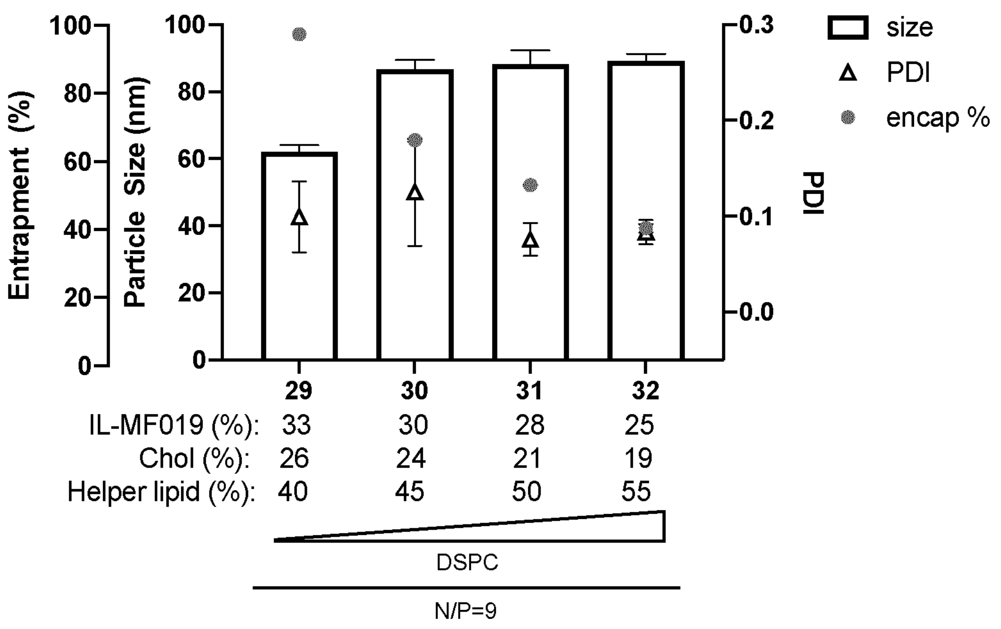
FIG. 2M shows entrapment %, particle size and PDI of lipid nanoparticles (top graph) containing a DNA vector encoding luciferase as a function of the amount of DSPC neutral lipid (40-55 mol %). LNP formulations 29 to 32 comprise varying amounts of MF019 ionizable lipid, cholesterol and DSPC at the mol % indicated and PEG-DMG at 1 mol % at a nitrogen-to-phosphate ratio (N/P) of 9. Details of the lipid formulations are shown in Table 2.
Figure 2N:
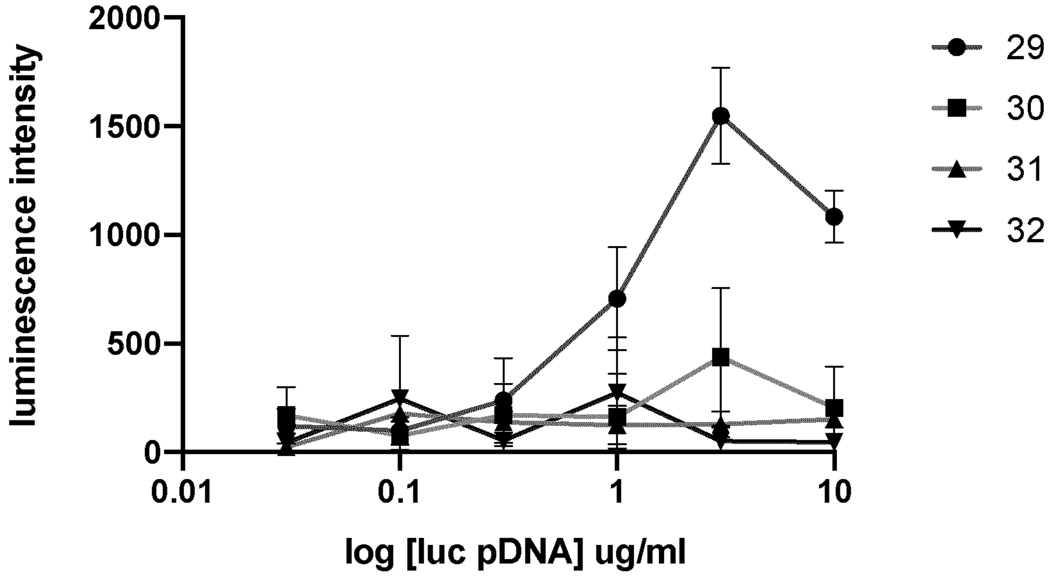
FIG. 2N shows luminescence intensity after addition of LNP formulations 29 to 32 to Huh7 cells over a range of 0.03-10 μg/mL DNA encoding luciferase. Details of the lipid formulations are shown in Table 2.
Figure 3A:
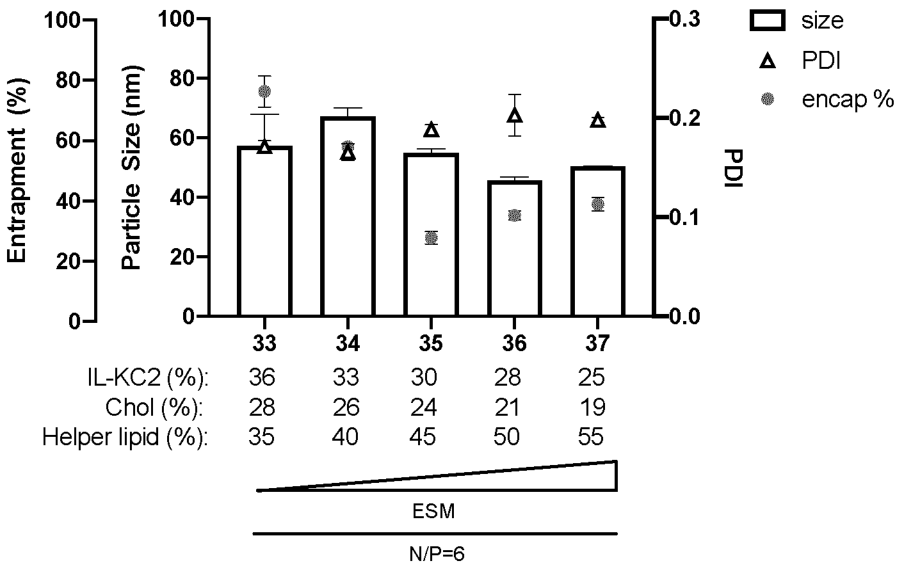
FIG. 3A shows entrapment %, particle size and PDI of lipid nanoparticles (top graph) containing a DNA vector encoding luciferase as a function of the amount of egg sphingomyelin (ESM) neutral lipid (35-55 mol %). LNP formulations 33 to 37 comprise varying amounts of KC2 ionizable lipid, cholesterol and ESM at the mol % indicated and PEG-DMG at 1 mol % at an N/P of 6. Details of the lipid formulations are shown in Table 3.
Figure 3B:
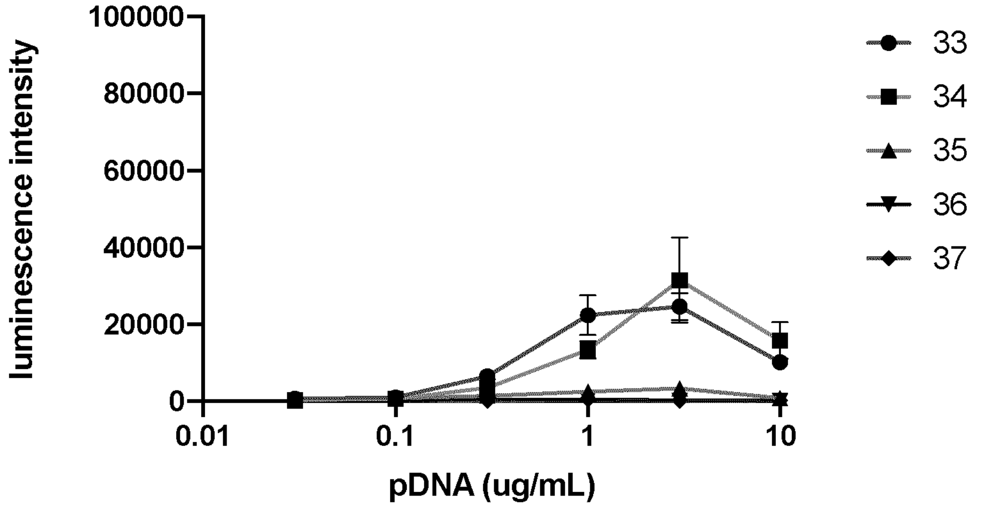
FIG. 3B shows luminescence intensity after addition of LNP formulations 33 to 37 to Huh7 cells over a range of 0.03-10 μg/mL DNA encoding luciferase. Details of the lipid formulations are shown in Table 3.
Figure 3C:
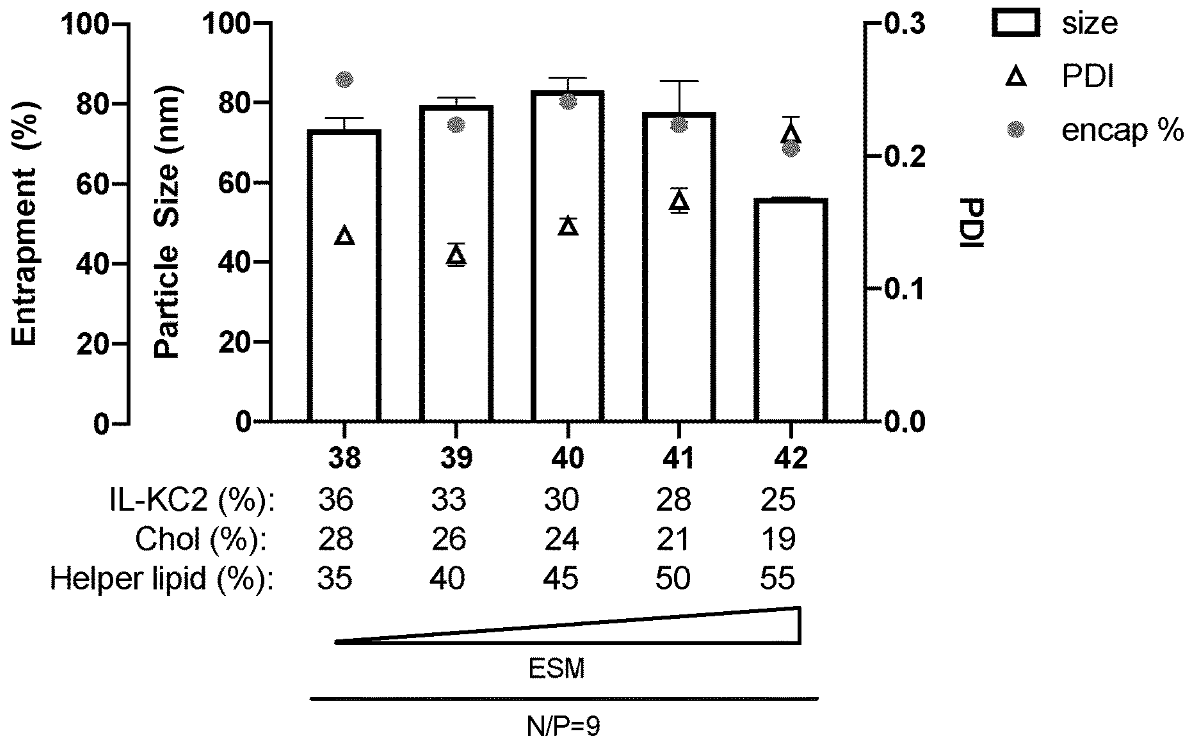
FIG. 3C shows entrapment %, particle size and polydispersity index (PDI) of lipid nanoparticles (top graph) containing a DNA vector encoding luciferase as a function of the amount of ESM neutral lipid (35-55 mol %). LNP formulations 38 to 42 comprise varying amounts of KC2 ionizable lipid, cholesterol and ESM at the mol % indicated and PEG-DMG at 1 mol % at an N/P of 9. Details of the lipid formulations are shown in Table 3.
Figure 3D:
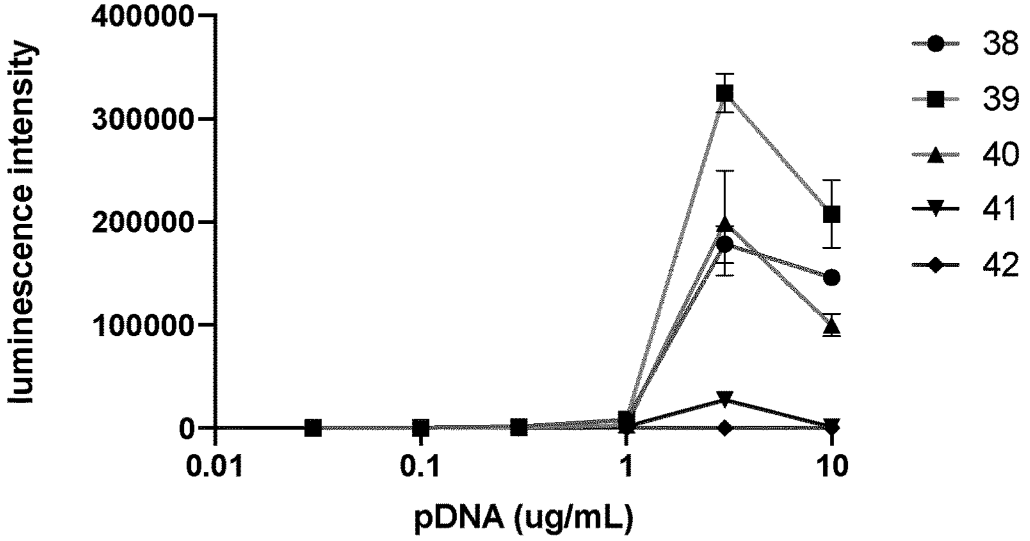
FIG. 3D shows luminescence intensity after addition of LNP formulations 38 to 42 to Huh7 cells over a range of 0.03-10 μg/mL DNA encoding luciferase. Details of the lipid formulations are shown in Table 3.

The formulations examined are presented in Table 1 below. The effect of increasing DOPC neutral lipid content on LNP size, PDI, encapsulation efficiency and transfection efficiency is shown in FIG. 1.

TABLE 1

Formulations examined with increasing DOPC neutral lipid content

| LNP Formulation Number | Ionizable Lipid mol % (MF019) | Neutral Lipid mol % (DOPC) | Chol mol % | PEG mol % | N/P |
|---|---|---|---|---|---|
| 1 | 33.15 | 40 | 25.85 | 1 | 6 |
| 2 | 30.34 | 45 | 23.66 | 1 | 6 |
| 3 | 27.53 | 50 | 21.47 | 1 | 6 |
| 4 | 24.72 | 55 | 19.28 | 1 | 6 |

Example 2: Effect of Increasing DSPC Neutral Lipid Content on LNP Size, PDI, Encapsulation Efficiency and Transfection Efficiency LNP formulations containing the ionizable lipid MF019 or KC2, neutral lipid DSPC, cholesterol, and 1 mol % PEG-DMG were prepared containing DNA vector encoding luciferase. The molar percentage of DSPC was increased from 20-55 mol %. Correspondingly, the ionizable lipid and cholesterol levels were decreased while maintaining a ratio of 1.3 mol/mol, respectively.

Table 2 below shows the lipid components used in each formulation. The effect of increasing DSPC neutral lipid content on LNP size, PDI, encapsulation efficiency and transfection efficiency is shown in FIGS. 2A-G.

TABLE 2

Formulations examined with increasing DSPC neutral lipid content

| FIG. | LNP Formulation Number | Ionizable Lipid mol % | Neutral Lipid mol % | Chol mol % | PEG mol % | N/P |
|---|---|---|---|---|---|---|
| 2A-B | 5 | 44.38 (KC2) | 20 (DSPC) | 34.62 | 1 | 6 |
| | 6 | 41.57 | 25 | 32.43 | 1 | 6 |
| | 7 | 38.77 | 30 | 30.23 | 1 | 6 |
| | 8 | 35.96 | 35 | 28.04 | 1 | 6 |
| 2C-D | 9 | 44.38 (KC2) | 20 (DSPC) | 34.62 | 1 | 9 |
| | 10 | 41.57 | 25 | 32.43 | 1 | 9 |
| | 11 | 38.77 | 30 | 30.23 | 1 | 9 |
| | 12 | 35.96 | 35 | 28.04 | 1 | 9 |
| 2E-F | 13 | 44.38 (MF019) | 20 (DSPC) | 34.62 | 1 | 6 |
| | 14 | 41.57 | 25 | 32.43 | 1 | 6 |
| | 15 | 38.77 | 30 | 30.23 | 1 | 6 |
| | 16 | 35.96 | 35 | 28.04 | 1 | 6 |
| 2G-H | 17 | 44.38 (MF019) | 20 (DSPC) | 34.62 | 1 | 9 |
| | 18 | 41.57 | 25 | 32.43 | 1 | 9 |
| | 19 | 38.77 | 30 | 30.23 | 1 | 9 |
| | 20 | 35.96 | 35 | 28.04 | 1 | 9 |
| 2I-J | 21 | 33.15 (KC2) | 40 (DSPC) | 25.85 | 1 | 6 |
| | 22 | 30.34 | 45 | 23.66 | 1 | 6 |
| | 23 | 27.53 | 50 | 21.47 | 1 | 6 |
| | 24 | 24.72 | 55 | 19.28 | 1 | 6 |
| 2K-L | 25 | 33.15 (MF019) | 40 (DSPC) | 25.85 | 1 | 6 |
| | 26 | 30.34 | 45 | 23.66 | 1 | 6 |
| | 27 | 27.53 | 50 | 21.47 | 1 | 6 |
| | 28 | 24.72 | 55 | 19.28 | 1 | 6 |
| 2M-N | 29 | 33.15 (MF019) | 40 (DSPC) | 25.85 | 1 | 9 |
| | 30 | 30.34 | 45 | 23.66 | 1 | 9 |
| | 31 | 27.53 | 50 | 21.47 | 1 | 9 |
| | 32 | 24.72 | 55 | 19.28 | 1 | 9 |

Example 3: Effect of Increasing Egg Sphingomyelin (ESM) Neutral Lipid on LNP Size, PDI, Encapsulation Efficiency and Transfection Efficiency LNP formulations containing the ionizable lipid KC2, neutral lipid ESM, cholesterol, and 1 mol % PEG-DMG were prepared containing DNA vector encoding luciferase. The molar percentage of ESM was increased from 35 to 55 mol %. Correspondingly, the ionizable lipid and cholesterol levels were decreased while maintaining a ratio of 1.3 mol/mol, respectively.

Table 3 below shows the lipid components used in each formulation. The effect of increasing ESM neutral lipid content on LNP size, PDI, encapsulation efficiency and transfection efficiency is shown in FIGS. 2A-G.

TABLE 3

Formulations examined with increasing ESM neutral lipid content

| FIG. | LNP Formulation Number | Ionizable Lipid mol % | Neutral Lipid mol % | Chol mol % | PEG mol % | N/P |
|---|---|---|---|---|---|---|
| 3A | 33 | 35.95 (KC2) | 35 (ESM) | 28.05 | 1 | 6 |
| | 34 | 33.15 | 40 | 25.85 | 1 | 6 |
| | 35 | 30.34 | 45 | 23.66 | 1 | 6 |
| | 36 | 27.53 | 50 | 21.47 | 1 | 6 |
| | 37 | 24.72 | 55 | 19.28 | 1 | 6 |

TABLE 3-continued

Formulations examined with increasing ESM neutral lipid content

| FIG. | LNP Formulation Number | Ionizable Lipid mol % | Neutral Lipid mol % | Chol mol % | PEG mol % | N/P |
|---|---|---|---|---|---|---|
| 3B | 38 | 35.95 (KC2) | 35 (ESM) | 28.05 | 1 | 9 |
| | 39 | 33.15 | 40 | 25.85 | 1 | 9 |
| | 40 | 30.34 | 45 | 23.66 | 1 | 9 |
| | 41 | 27.53 | 50 | 21.47 | 1 | 9 |
| | 42 | 24.72 | 55 | 19.28 | 1 | 9 |

Example 4: Suitable Method for In Vivo Analysis of GFP or Luciferase Gene Expression in the Liver, Spleen and/or Bone Marrow or a Disease Site at a Time Point 24 Hours or 48 Hours Post-Injection The following describes a suitable method for measuring in vivo expression of vector DNA in the liver, spleen, lung and/or bone marrow in a mouse model. As discussed previously, such method may be used to determine the expression level of reporter DNA (e.g. a gene) from a DNA vector relative to the Onpattro™ formulation.

The mice are divided into groups of two and receive intravenous (i.v.) injection of DNA vector encoding GFP or luciferase (Luc) delivered using LNPs based on Onpattro™, or a vector DNA lipid nanoparticle composition in question, and may use phosphate buffered saline (PBS) as a negative control. For biodistribution studies, LNPs entrapping DNA vector encoding GFP (or Luc) are labelled with 0.2 mol % DiD as a fluorescent lipid marker. Injections are performed at 3 mg/kg vector DNA dose and mice are sacrificed at 24 or 48 hours post injection (hpi). Mice are first anesthetized using a high dose of isofluorane followed by $CO_2$. Transcardiac perfusion is performed as follows: once the animals are unresponsive, a 5 cm medial incision is made through the abdominal wall, exposing the liver and heart. While the heart is still beating, a butterfly needle connected to a 30 ml syringe loaded with pre-warmed Hank's Balanced Salt Solution (HBSS, Gibco) is inserted into the left ventricle. Next, the liver is perfused with perfusion medium (HBSS, supplemented with 0.5 mM EDTA, Glucose 10 mM and HEPES 10 mM) at a rate of 3 mL/min for 10 min. Once liver swelling is observed, a cut is performed on the right atrium and perfusion is switched to digestion medium (DMEM, Gibco supplemented with 10% fetal bovine serum (FBS, Gibco) and 1% penicillin streptomycin (Gibco) and 0.8 mg/mL Collagenase Type IV, Worthington) at 3 mL/min for another 10 min. At the end of the perfusion of the entire system, as determined by organ blanching, the whole liver and spleen are dissected and transferred to 50 mL Falcon™ tubes containing 10 mL ice cold (4° C.) perfusion media and placed on ice.

Next, isolation of hepatocytes is performed following density gradient-based separation. Spleens and femurs are also harvested to isolate splenocytes and bone marrow cells. Briefly, the liver is transferred to a Petri dish containing digestion medium, minced under sterile conditions, and incubated for 20 min at 37° C. with occasional shaking of the plate. Cell suspensions are then filtered through a 40 μm mesh cell strainer to eliminate any undigested tissue remnants. Primary hepatocytes are separated from other liver residing cells by low-speed centrifugation at 500 rpm with no brake. The pellet containing mainly hepatocytes was collected, washed at 5000 rpm for 5 min and kept in 4° C. Femurs are centrifuged 10,000 g in a microcentrifuge for 10 seconds to collect the marrow that is resuspended in ACK lysis buffer for 1 min to deplete the red blood followed by washing with ice-cold PBS.

Phenotypic detection of hepatocytes is then performed using monoclonal antibodies to assess LNP delivery and DNA expression. Cellular uptake and GFP or luciferase expression is also detected in splenocytes and bone marrow cells immediately after isolation. Here, the spleen is dissected and placed into a 40 μm mesh cell and mashed through a cell strainer into a petri dish using a plunger end of a syringe. The suspended cells are transferred to a 15 mL Falcon™ tube and centrifuged at 1,000 rpm for 5 minutes. The pellet is resuspended in 1 mL ACK lysis buffer (Invitrogen™) to lyse the red blood cells and aliquoted in FACS buffer. Cell aliquots are resuspended in 300 μL FACS staining buffer (FBS 2%, Sodium Azide 0.1% and ethylenediaminetetraacetic acid (EDTA 1 mM)) followed by staining with fluorescence tagged antibodies. Prior to staining, cells are first labeled with anti-mouse CD16/CD32 (mouse Fc blocker, Clone 2.4$G^2$) (AntibodyLab™, Vancouver, Canada) to reduce background. Hepatocytes are detected following staining with primary mouse antibody detecting ASGR1 (8D7, Novus Biologicals) followed by goat polyclonal secondary antibody to mouse IgG2a labeled to PE-Cy7 (BioLegend™).

Detection of hepatocytes, splenocytes, bone marrow cells and cells from a target disease site (e.g., tumor) or other organ as applicable is carried out using an LSRII flow cytometer and a FACSDiva™ software and analyzed by FlowJo™ following acquisition of 1000000 events after gating on viable cell populations. LNP-vector delivery or transfection efficacy is assessed based on the relative mean fluorescence intensity of DiD or GFP positive cells, respectively, measured on histograms obtained from gated cell populations.

Statistical analyses are performed using a two-tailed Student's t-test, where groups are compared. The type (paired or two-sample equal variance-homoscedastic), is determined based on the variation of the standard deviation of two populations. $P<0.05$ is accepted as statistically significant (*$P<0.05$).

The above method can be adapted by those of skill in the art to assess increases in DNA expression in a disease site or an organ besides liver, spleen or bone marrow at any one time point greater than 24 or 48 hours post-injection in a mouse model as compared to a lipid nanoparticle encapsulating the DNA vector with an Onpattro-type formulation.

For disease sites, the tissue is excised, cut into smaller pieces and subjected to dispase and collagenase to break down connective tissue. The tissue is then mashed through a 40 μm cell strainer into a petri dish using a plunger end of a syringe. The suspended cells are transferred to a 15 mL Falcon™ tube and centrifuged at 1,000 rpm for 5 minutes. Cell aliquots are resuspended in 300 μL FACS staining buffer (FBS 2%, Sodium Azide 0.1% and ethylenediaminetetraacetic acid (EDTA 1 mM)) and subjected to flow cytometry analysis as described above.

For lung tissue, 10 mL of digestion medium is prepared by adding 1 mL of collagenase/hyaluronidase and 1.5 mL of DNase I Solution (1 mg/mL) to 7.5 mL of RPMI 1640 Medium and warmed to room temperature. Harvested lung tissue in PBS/2% FBS is transferred into a dish without medium and minced into a homogenous paste (<1 mm in size) using a razor blade or scalpel. The minced lung tissue is then transferred into a tube containing 10 mL of digestion medium and incubated at 37° ° C. for 20 minutes on a shaking platform. A 70 μm nylon mesh strainer is placed over a 100 mm dish and the digested lung tissue is pushed through the strainer with the rubber end of a syringe plunger to obtain a cell suspension. A new 70 μm nylon mesh strainer is then placed over a 50 mL conical tube and the cell suspension is filtered through and strainer rinsed with recommended medium. The solution is centrifuged at 300×g for six minutes at room temperature with the brake on low, followed by careful removal and discard of the supernatant. 20 mL of ammonium chloride solution is added to the cell pellet, followed by incubation at room temperature for five minutes. Recommended medium is added to achieve a final volume of 50 mL and the solution centrifuged at 300×g for six minutes at room temperature with the brake on low, followed by careful removal and discard of the supernatant. The cells are resuspended in recommended medium at the required cell concentration and subjected to flow cytometry analysis as described above.

Example 5: Results of In Vivo Analysis of Biodistribution and Gene Expression from Vector DNA-LNP in the Liver, Spleen and/or Bone Marrow at 24 Hours Post-Injection The following LNPs containing vector DNA encoding luciferase and DiD lipid marker were prepared as described in the Materials and Methods to assess in vivo biodistribution and gene expression from the vector DNA.

TABLE 4

Lipid nanoparticle formulations assessed for in vivo biodistribution and expression of vector DNA luciferase in spleen, liver and lungs

| FIG. | LNP | Ionizable lipid mol % | Neutral lipid mol % | Chol mol % | PEG-DMG mol % | DiD mol % | N/P |
|---|---|---|---|---|---|---|---|
| 4A | | Phosphate buffered saline (PBS) | | | | | |
| 4B | A | 50 nKC2 | 10 DSPC | 38.25 | 1 | 0.75 | 6 |
| 4C | B | 27.53 nKC2 | 50 DSPC | 20.72 | 1 | 0.75 | 6 |
| 4D | C | 35.95 nKC2 | 35 ESM | 27.30 | 1 | 0.75 | 9 |
| 4E | D | 33.15 MF019 | 40 DSPC | 25.10 | 1 | 0.75 | 6 |
| 4F | E | 33.15 MF019 | 40 DSPC | 25.10 | 1 | 0.75 | 9 |

nKC2 is an ionizable lipid described in PCT/CA2022/050853 filed on May 26, 2022 and MF019 is an ionizable lipid described in PCT/CA2022/050042 filed on Jan. 12, 2022.

Figure 4A:
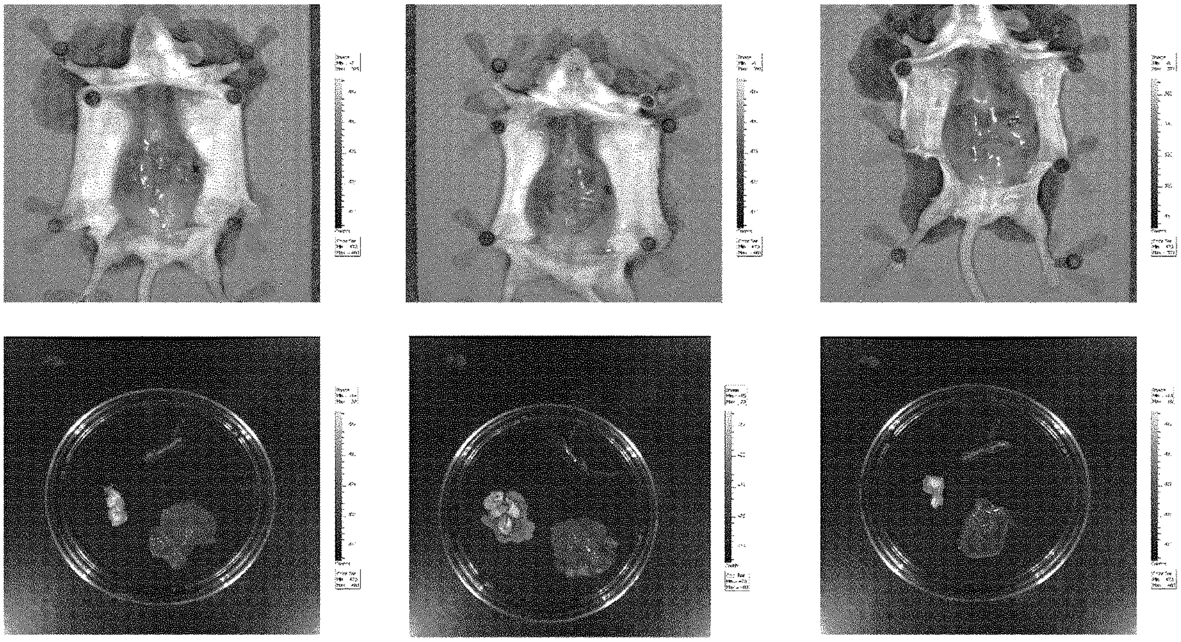
FIG. 4A shows images of biodistribution in CD-1 mice (n=3) that were administered with phosphate buffered saline (PBS). The images were taken at 24 hours post injection.
Figure 4B:
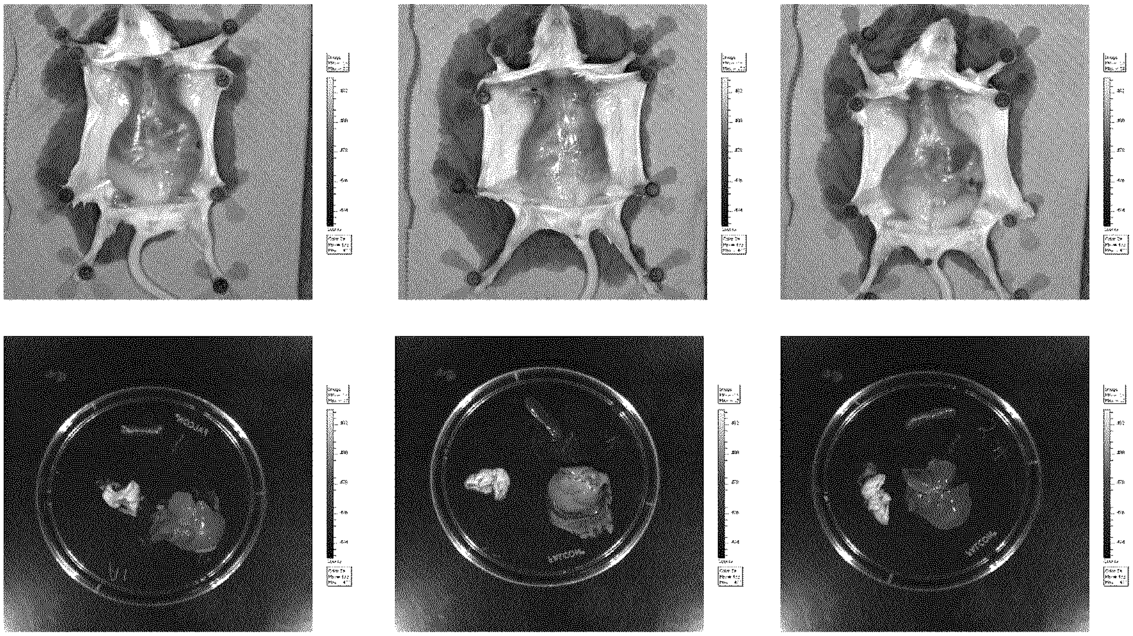
FIG. 4B shows images of biodistribution in CD-1 mice that were administered with a lipid nanoparticle encapsulating vector DNA encoding luciferase and composed of norKC2/DSPC/Chol/PEG-DMG at molar ratios of 50/10/38.25/1 (Formulation A) and 0.75 mol % of a lipid marker, DiD. The nitrogen-to-phosphate ratio (N/P) was 6. The images were taken at 24 hours post injection.

The tissue biodistribution results are shown in FIGS. 4A to 4F. The PBS control and formulation A having only 10 mol % DSPC exhibited no tissue DiD-lipid uptake as visualized by measuring DiD fluorescence (FIGS. 4A and 4B).

Figure 4C:
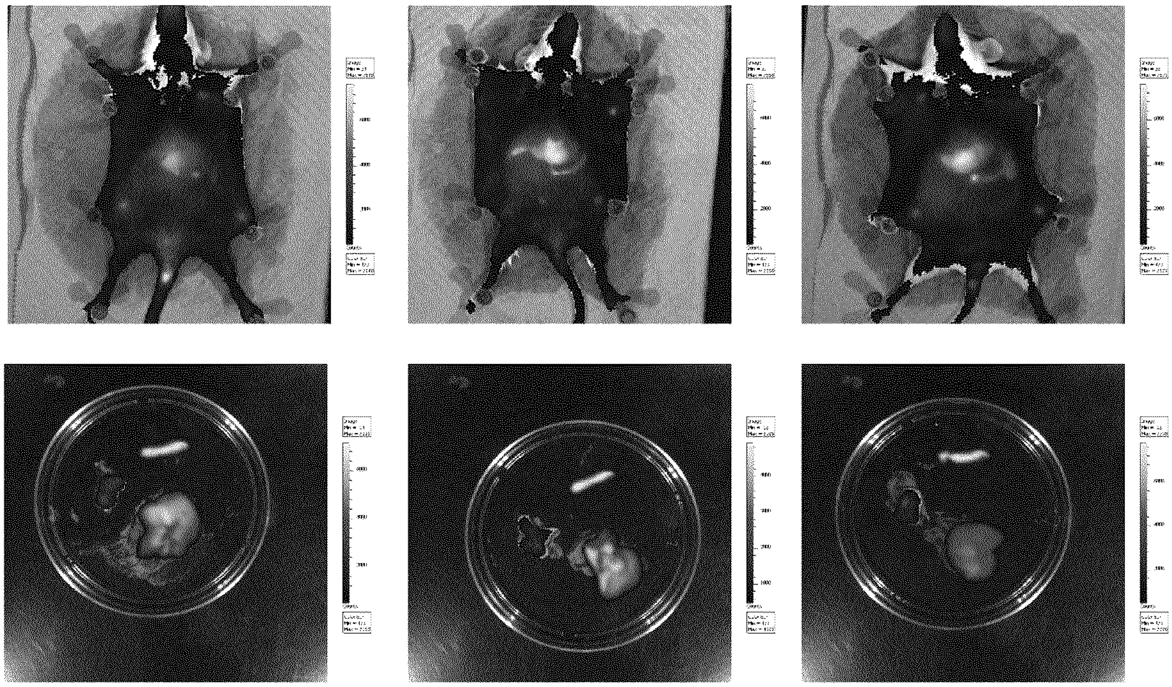
FIG. 4C shows images of biodistribution CD-1 in mice that were administered with a lipid nanoparticle encapsulating vector DNA encoding luciferase and composed of norKC2/DSPC/Chol/PEG-DMG at molar ratios of 27.53/50/20.72/1 (Formulation B) and 0.75 mol % of a lipid marker, DiD. The N/P was 6 and the images were taken at 24 hours post injection.
Figure 4D:
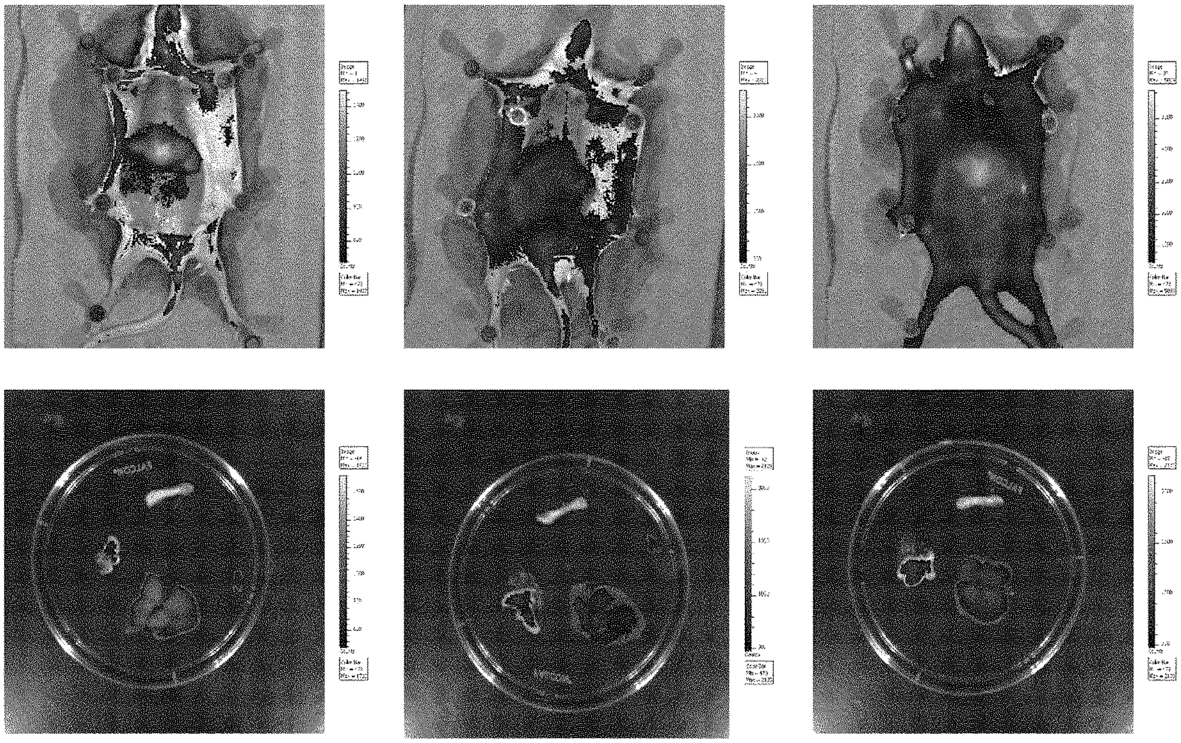
FIG. 4D shows images of biodistribution CD-1 in mice that were administered with a lipid nanoparticle encapsulating vector DNA encoding luciferase and composed of norKC2/ESM/Chol/PEG-DMG at molar ratios of 35.95/35/27.30/1 (Formulation C) and 0.75 mol % of a lipid marker, DiD. The N/P was 9 and the images were taken at 24 hours post injection.

By contrast, formulation B having 50 mol % DSPC exhibited a strong spleen and liver DiD-lipid uptake, as well as some uptake in the lungs (FIG. 4C). Formulation C having 35 mol % egg sphingomyelin (ESM) had strong uptake in the spleen with more modest uptake in the lungs and liver (FIG. 4D).

Figure 4E:
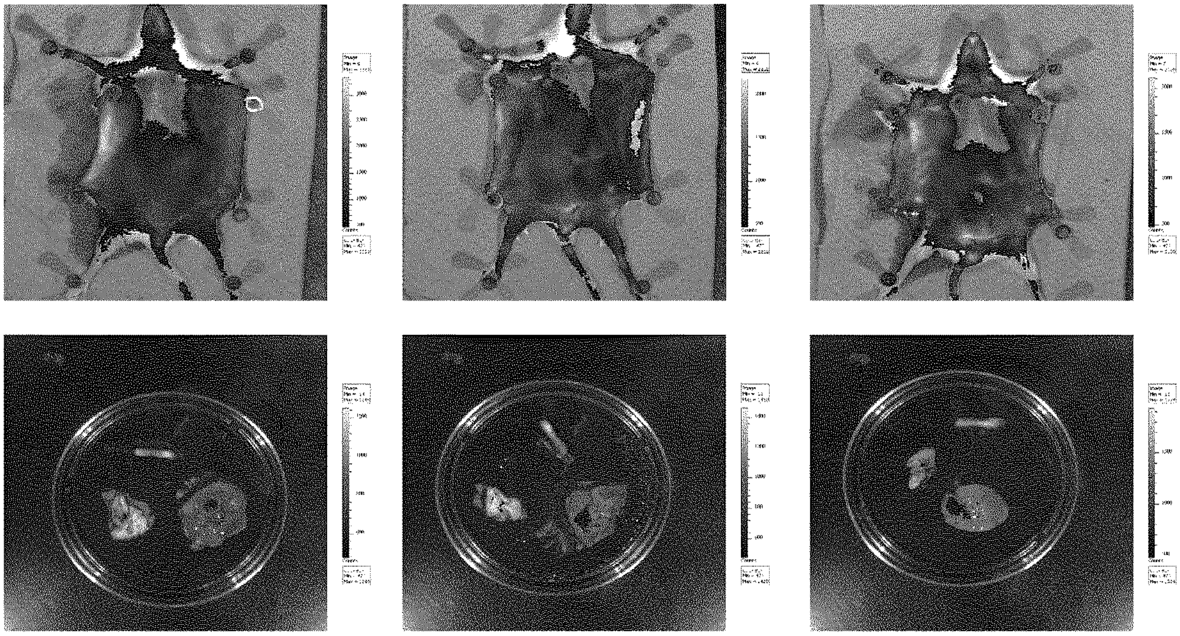
FIG. 4E shows images of biodistribution in CD-1 mice that were administered with a lipid nanoparticle encapsulating vector DNA encoding luciferase and composed of MF019/DSPC/Chol/PEG-DMG at molar ratios of 33.15/40/25.10/1 (Formulation D) and 0.75 mol % of a lipid marker, DiD. The N/P was 6 and the images were taken at 24 hours post injection.
Figure 4F:
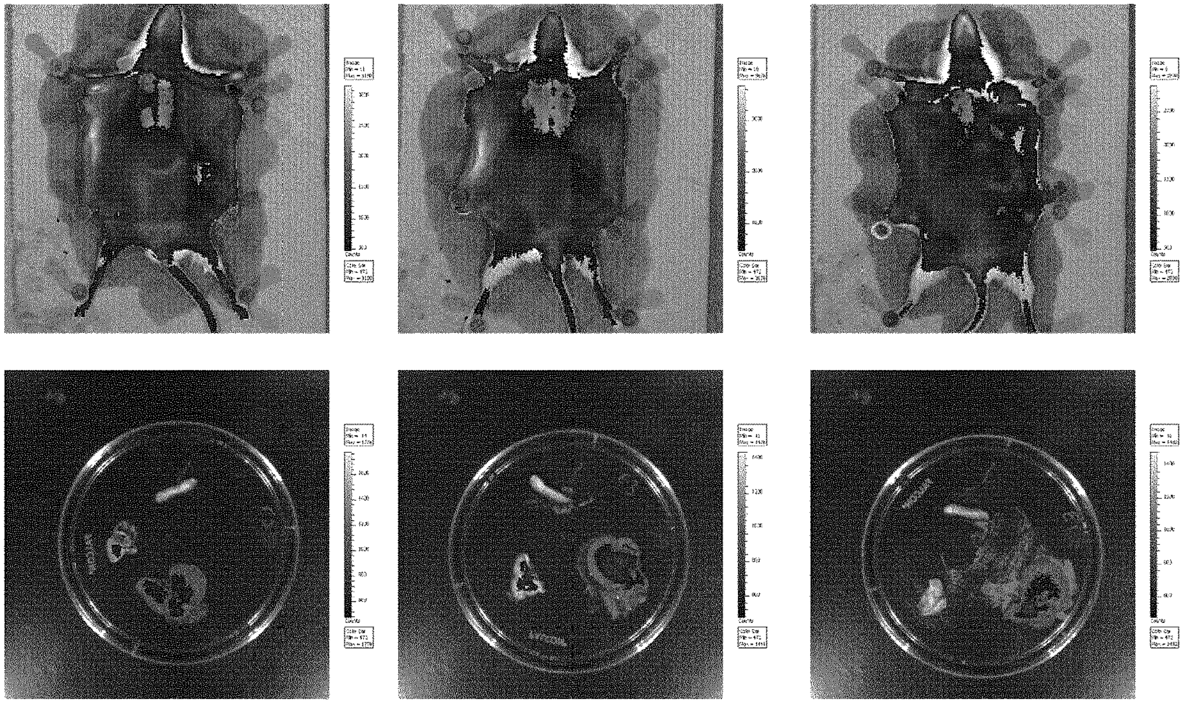
FIG. 4F shows images of biodistribution in CD-1 mice that were administered with a lipid nanoparticle encapsulating vector DNA encoding luciferase and composed of MF019/DSPC/Chol/PEG-DMG at molar ratios of 33.15/40/25.10/1 (Formulation E) and 0.75 mol % of a lipid marker, DiD. The N/P was 9 and the images were taken at 24 hours post injection.

Formulation D having 40 mol % DSPC showed high uptake in the spleen as measured by DiD-lipid uptake, and more modest amounts of uptake in the lungs and liver (FIG. 4E). Formulation E having the same lipid composition as formulation D, but with a higher N/P exhibited high uptake in the spleen with lesser uptake of DiD-lipid in the lungs and liver (FIG. 4F).

Figure 5A:
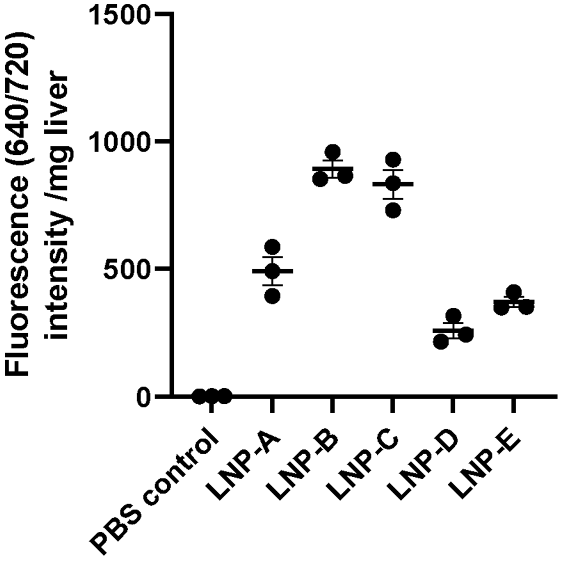
FIG. 5A shows fluorescence intensity of the lipid marker, DiD, in tissue homogenate from the liver of CD-1 mice (reported as fluorescence intensity/mg liver) at 24 hours post injection for PBS control and lipid nanoparticle formulations A-E encapsulating vector DNA encoding luciferase. The lipid nanoparticle formulations are provided in Table 4.
Figure 5B:
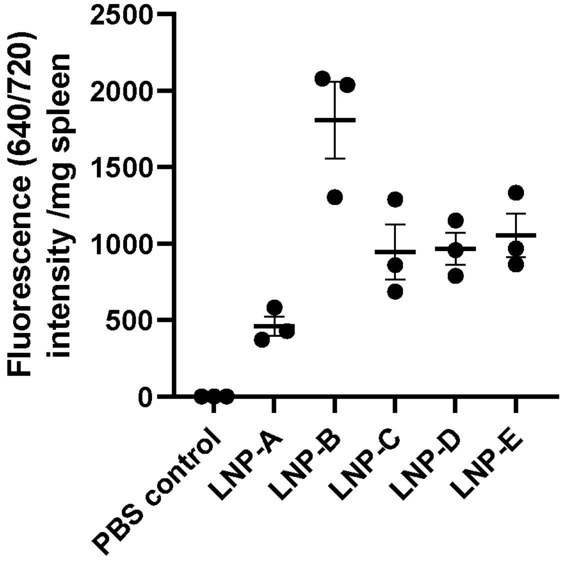
FIG. 5B shows fluorescence intensity of the lipid marker, DiD, in the spleen of CD-1 mice (reported as fluorescence intensity/mg spleen) at 24 hours post injection for PBS control and lipid nanoparticle formulations A-E encapsulating vector DNA encoding luciferase. The lipid nanoparticle formulations are provided in Table 4.
Figure 5C:
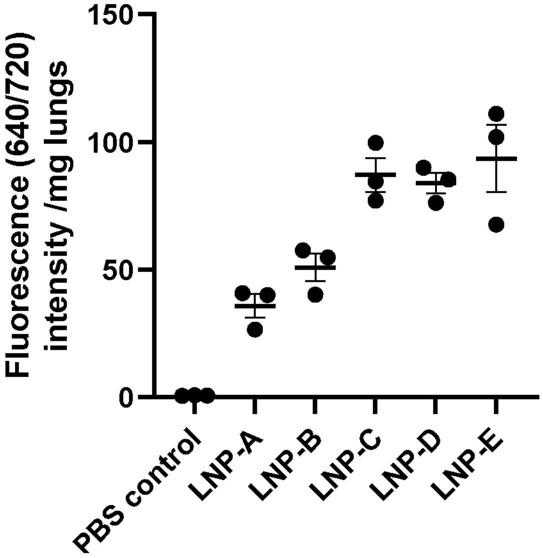
FIG. 5C shows fluorescence intensity of the lipid marker, DiD, in tissue homogenate from the lungs of CD-1 mice (reported as fluorescence intensity/mg lungs) at 24 hours post injection for PBS control and lipid nanoparticle formulations A-E encapsulating vector DNA encoding luciferase. The lipid nanoparticle formulations are provided in Table 4.

Tissue homogenate data for phosphate buffered saline (PBS) and formulations A-E (Table 4) from the liver, spleen and lung is shown in FIGS. 5A-C. In the spleen and lungs, formulation A having the lowest level of neutral lipid (10 mol % DSPC) had low levels of biodistribution in both organs (FIG. 5A and FIG. 5B). By contrast, formulations B-E having elevated levels of neutral lipid (>35 mol % neutral lipid) exhibited the strongest signals in the spleen and lungs (FIG. 5A and FIG. 5B).

In the liver, formulation A having the lowest level of neutral lipid (10 mol % DSPC) had a moderate signal in the liver. Formulation A and B (50 mol % DSPC and 35 mol % ESM) had the strongest signal in the liver, while formulation D and E had comparatively less fluorescent intensity in the liver.

Figure 6A:
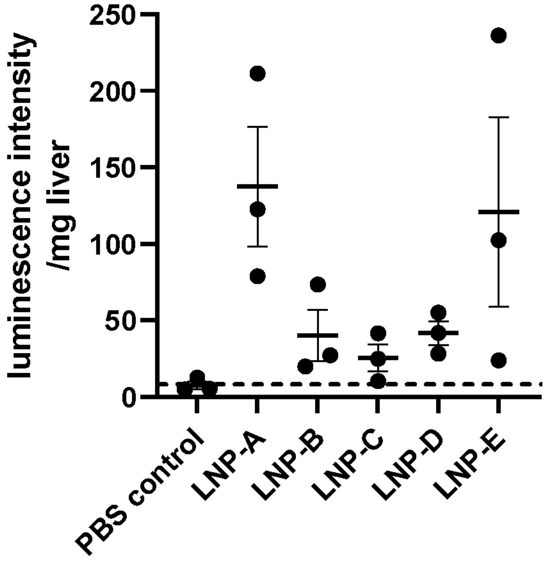
FIG. 6A shows luminescence intensity in tissue homogenate from the liver of CD-1 mice (reported as fluorescence intensity/mg liver) at 24 hours post injection for PBS control and lipid nanoparticle formulations A-E encapsulating vector DNA encoding luciferase. The lipid nanoparticle formulations are provided in Table 4.
Figure 6B:
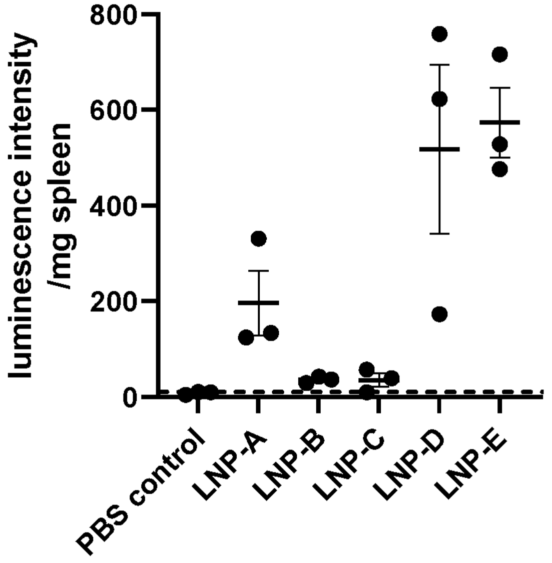
FIG. 6B shows luminescence intensity in tissue homogenate from the spleen of CD-1 mice (reported as fluorescence intensity/mg spleen) at 24 hours post injection for PBS control and lipid nanoparticle formulations A-E encapsulating vector DNA encoding luciferase. The lipid nanoparticle formulations are provided in Table 4.
Figure 6C:
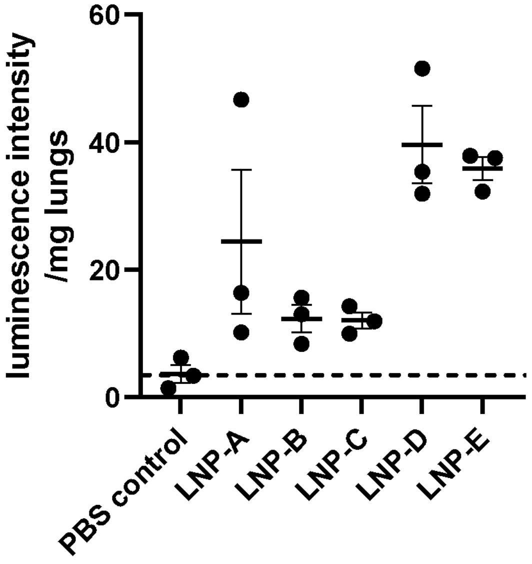
FIG. 6C shows luminescence intensity in tissue homogenate from the lungs of CD-1 mice (reported as fluorescence intensity/mg lungs) at 24 hours post injection for PBS control and lipid nanoparticle formulations A-E encapsulating vector DNA encoding luciferase. The lipid nanoparticle formulations are provided in Table 4.

In vivo gene expression of pDNA encoding luciferase was measured in the liver, spleen and lungs for PBS control and formulations A-E of Table 4 above. The results are shown in FIGS. 6A, 6B and 6C. Formulations D and E having 40 mol % DSPC had the best extrahepatic delivery relative to the other formulations tested.

In this non-limiting example, a decreased accumulation of DSPC in the liver was observed relative to egg sphingomyelin (FIG. 5). Thus, in some embodiments, it may be advantageous to select an LNP comprising elevated levels of DSPC over the same LNP comprising ESM if accumulation beyond the liver is desired.

Example 6: Vector DNA Tumour Expression Data for Lipid Nanoparticles Having Elevated Levels of Neutral Lipid Vs. Standard LNPs Having 10 Mol % DSPC The following lipid nanoparticles having 10 mol % and 40 mol % neutral lipid and encapsulating a vector DNA encoding a secreted protein were prepared as described in the Materials and Methods above.

TABLE 5

Lipid nanoparticle formulations containing vector DNA for a secreted protein assessed for tumour expression

| LNP | Ionizable lipid and mol % | Neutral lipid mol % | Chol mol % | PEG mold % | N/P |
|---|---|---|---|---|---|
| A | 50 nKC2 | 10 DSPC | 39 | 1 | 6 |
| E | 33 MF019 | 40 DSPC | 26 | 1 | 6 |
| J | 33 MF019 | 40 DSPC | 26 | 1 | 9 |

nKC2 is an ionizable lipid described in PCT/CA2022/050853 filed on May 26, 2022 and MF019 is an ionizable lipid described in PCT/CA2022/050042 filed on Jan. 12, 2022.

Figure 7:
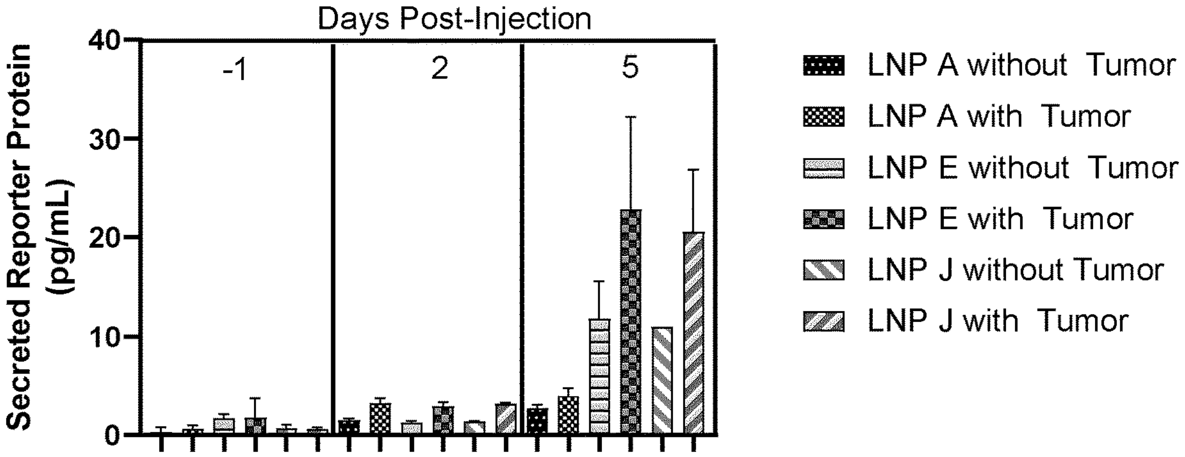
FIG. 7 shows secreted reporter protein (pg/mL) at −1, 2 and 5 days post-injection for lipid nanoparticle formulations encapsulating vector DNA encoding the reporter protein. The lipid nanoparticles were composed of norKC2/DSPC/Chol/PEG-DMG (50/10/39/1 mol:mol; LNP A) having an N/P of 6; MF019/DSPC/Chol/PEG-DMG (33/40/26/1 mol:mol; LNP E) having an N/P of 6; and MF019/DSPC/Chol/PEG-DMG (33/40/26/1 mol:mol; LNP J) having an N/P of 9. Formulations are also shown in Table 5. Each formulation (A, E and J) was injected into mice without and with tumours. The data set for each time point from left to right for −1, 2 and 5 days is LNP A without tumour; LNP A with tumour; LNP E without tumour; LNP E with tumour; LNP J without tumour and LNP J with tumour.

Mice with and without tumours were injected with each formulation in Table 5 above. The results are shown in FIG. 7. The data in the FIG. 7 bar graph is arranged into three groups: Group 1 is the −1 day post-injection data in the left-most third of the bar graph; Group 2 is the 2 day post-injection in the middle third of the graph; and Group 3 is the 5 day post-injection data in the right-most third of the bar graph.

The conventional four-component LNP having 10 mol % DSPC (LNP formulation A) had comparable levels of secreted protein measured in the blood at 2 and 5 days post-administration for both tumour-bearing and non-tumour bearing mice (first and second bars in 2 and 5 days post-injection groups).

By comparison, LNPs having 40 mol % DSPC (formulations E and J) had elevated levels of secreted protein in blood of tumour-bearing mice relative to blood samples taken from non-tumour bearing mice at both day 2 and day 5 post-injection.

These results support that the LNP formulations having elevated neutral lipid content reached a distal tumour site. Further, the higher levels of secreted protein in tumour-bearing vs. non-tumour bearing mice indicates that the vector DNA encoding the protein was delivered to the rapidly dividing cells of the distal tumour site and translated into protein.

Example 7: Lipid Nanoparticles Having Elevated Levels of Neutral Lipid have a Unique Morphology Cryo-TEM images of lipid nanoparticles composed of MF019/DSPC/Chol/PEG-DMG (33/40/26/1 mol:mol; LNP E of Table 5) encapsulating a vector DNA encoding the reporter protein and lipid nanoparticles composed of norKC2/DSPC/chol/PEG-DMG (27.53/50/20.72/1 mol:mol; LNP B of Table 4) encapsulating a vector DNA encoding luciferase were obtained.

Figure 8A:
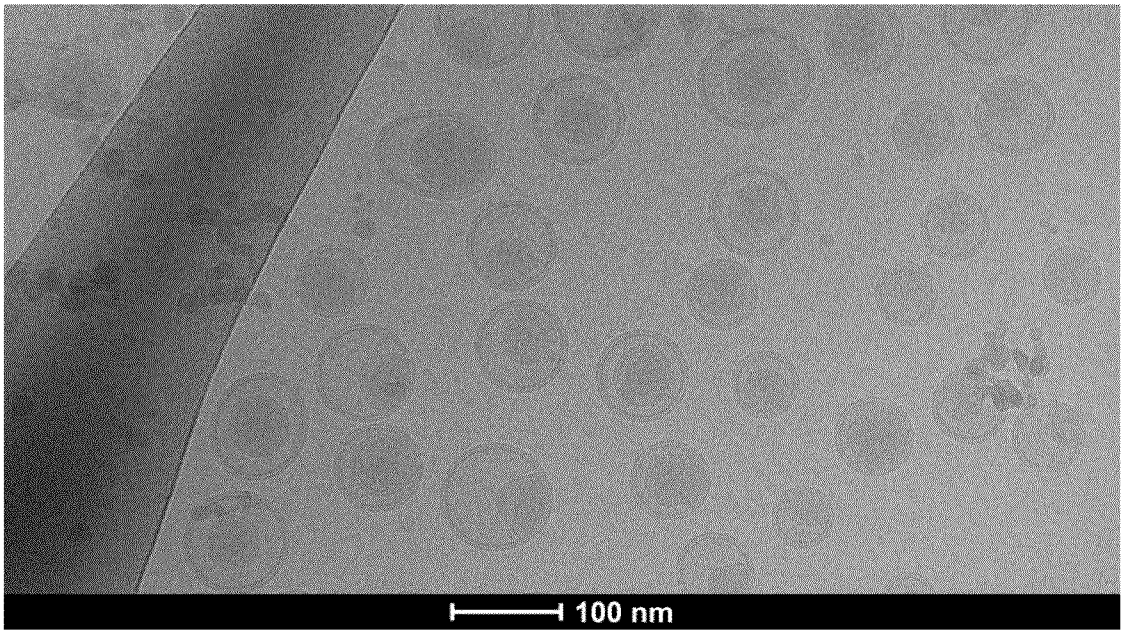
FIG. 8A shows cryo-TEM images of lipid nanoparticles composed of MF019/DSPC/Chol/PEG-DMG (33/40/26/1 mol:mol; LNP E of Table 5) encapsulating a vector DNA encoding the reporter protein and having an N/P of 6.
Figure 8B:
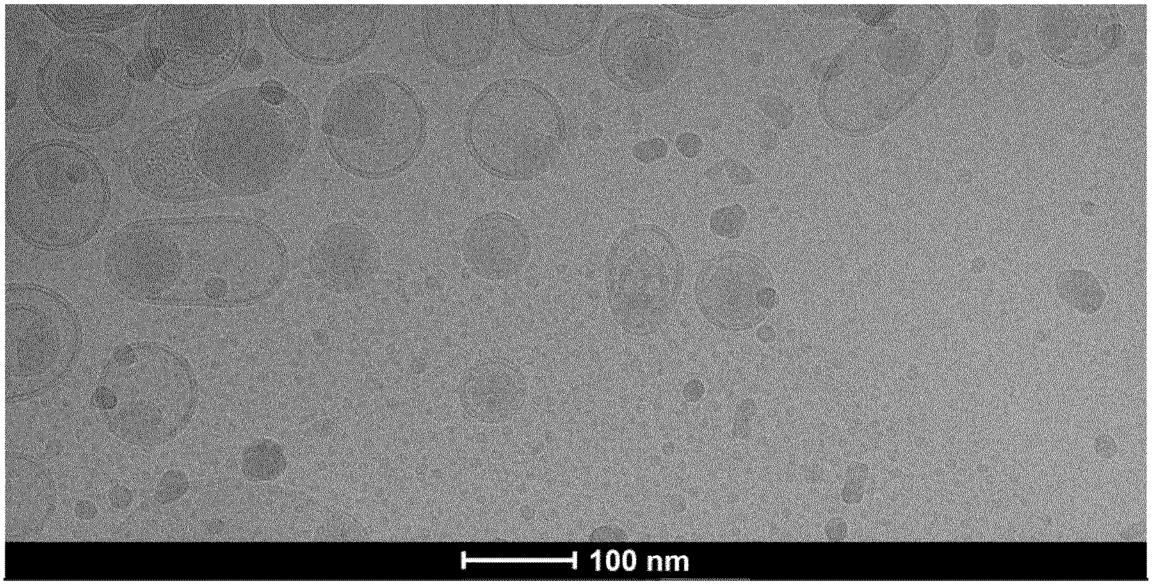
FIG. 8B shows cryo-TEM images of lipid nanoparticles composed of norKC2/DSPC/Chol/PEG-DMG (20.72/50/20.72/1 mol:mol; LNP B of Table 4) encapsulating a vector DNA encoding luciferase and having an N/P of 6.

The images for each formulation are shown in FIGS. 8A and 8B.

The images of the lipid nanoparticle having encapsulated DNA vector with high levels of neutral lipid (ESM and DSPC) have a morphology in which there is an electron dense region that is contained within the bilayer. The core, in turn, is surrounded by a structure consistent with a lipid bilayer as shown in FIGS. 8A and 8B. The morphology, which is unique to LNPs having elevated neutral lipid, may provide the LNPs with the improved in vivo delivery properties to target sites, such as sites with rapidly dividing cells (such as a distal tumour site or embryo) or the liver, spleen and/or lungs as observed in the previous examples.

Although the invention has been described and illustrated with reference to the foregoing examples, it will be apparent that a variety of modifications and changes may be made without departing from the invention.

The invention claimed is:

1. A lipid nanoparticle comprising encapsulated DNA vector and 35 to 60 mol % of a neutral lipid comprising or consisting of a phosphatidylcholine lipid, a cationic lipid at from 15 mol % to 45 mol %, at least one of a sterol and a hydrophilic polymer-lipid conjugate, and a combined sterol and neutral lipid content of at least 55 mol %, the lipid nanoparticle having an amine-to-phosphate charge ratio (N/P) from 3 to 15 and comprising a core having an electron dense region and an aqueous portion as determined by cryogenic transmission electron microscopy, the electron dense region being visualized by the cryogenic transmission electron microscopy as a dark region relative to the aqueous portion, the core surrounded at least partially by a lipid layer and the lipid nanoparticle exhibiting at least a 10% increase in DNA expression in a disease site or in the liver, spleen and/or bone marrow at any one time point greater than 24 or 48 hours post-injection as compared to a lipid nanoparticle encapsulating the DNA vector with a formulation of ionizable lipid/DSPC/cholesterol/PEG-lipid at 50/10/38.5/1.5, mol:mol, wherein the DNA expression is measured in an animal model by detection of a green fluorescent protein (GFP), wherein each mol % is based on a total lipid content in the lipid nanoparticle.

2. The lipid nanoparticle of claim 1, wherein the sterol is present and is cholesterol; and the hydrophilic polymer-lipid conjugate is present and wherein the content is from 0.5 mol % to 1.8 mol % of the total lipid.

3. The lipid nanoparticle of claim 1 wherein the lipid nanoparticle further exhibits at least a 10% increase in gene expression in a disease site or in the liver, spleen, lung and/or bone marrow at any one time point greater than 24 or 48 hours post-injection as compared to a lipid nanoparticle encapsulating the DNA vector with a formulation of ionizable lipid/DSPC/cholesterol/PEG-lipid at 50/10/38.5/1.5, mol:mol, wherein the gene expression is measured in an animal model by detection of luciferase.

4. The lipid nanoparticle of claim 1, wherein the phosphatidylcholine lipid is distearoylphosphatidylcholine (DSPC), dioleoylphosphatidylcholine (DOPC), 1-palmitoyl-2-oleoyl-phosphatidylcholine (POPC) or dipalmitoylphosphatidylcholine (DPPC).

5. The lipid nanoparticle of claim 1, wherein the lipid layer comprises at least a bilayer.

6. The lipid nanoparticle of claim 1, wherein the neutral lipid content is between 35 mol % and 50 mol %.

7. The lipid nanoparticle of claim 1, wherein the neutral lipid content is between 40 mol % and 60 mol %.

8. The lipid nanoparticle of claim 1, wherein the electron dense region is denser than the aqueous portion as visualized by cryogenic electron microscopy.

9. The lipid nanoparticle of claim 8, wherein the lipid nanoparticle is part of a preparation of lipid nanoparticles, and wherein the electron dense region of at least 20% of the lipid nanoparticles are either (i) enveloped by the aqueous portion, or (ii) is partially surrounded by the aqueous portion and wherein a portion of a periphery of the electron dense region is contiguous with the lipid layer, as visualized by cryogenic electron microscopy.

10. The lipid nanoparticle of claim 1, wherein at least a portion of the DNA vector is encapsulated in the electron dense region or the lipid layer.

11. The lipid nanoparticle of claim 1, wherein the lipid nanoparticle is part of a preparation of lipid nanoparticles and wherein at least 20% of the lipid nanoparticles as visualized by cryogenic electron microscopy are non-spherical in shape and wherein the length of the particle is greater than the width of the particle.

12. The lipid nanoparticle of claim 1, wherein the cationic lipid is an ionizable amino lipid.

13. The lipid nanoparticle of claim 1, wherein the hydrophilic polymer-lipid conjugate is a polyethyleneglycol-lipid conjugate.

14. The lipid nanoparticle of claim 1, wherein the sterol is present at from 15 mol % to 50 mol % based on the total lipid present in the lipid nanoparticle.

15. The lipid nanoparticle of claim 1, wherein the sterol is present at from 18 mol % to 45 mol % based on the total lipid present in the lipid nanoparticle.

16. The lipid nanoparticle of claim 1, wherein the disease site is a tumor.

17. A method for in vivo delivery of DNA vector to a bodily site in a mammalian subject, the method comprising:

administering to the mammalian subject a lipid nanoparticle of claim 1.

18. The method of claim 17, wherein the lipid nanoparticle treats the bodily site that comprises cells that are dividing at a rate that is at least 30% greater than surrounding parenchymal cells.

19. The method of claim 17, wherein the mammalian subject is a fetus.

20. The method of claim 17, wherein the lipid nanoparticle is delivered to spleen, bone marrow or liver.

21. The method of claim 17, wherein the lipid nanoparticle treats or prevents a viral infection.

22. The method of claim 17, wherein the bodily site ais a cancer.

23. The method of claim 17, wherein the lipid nanoparticle treats cardiovascular disease.

24. The method of claim 17, wherein the lipid nanoparticle treats a congenital disease or disorder.

* * * * *